(12) United States Patent
Chen et al.

(10) Patent No.: US 10,202,462 B2
(45) Date of Patent: Feb. 12, 2019

(54) BI-SPECIFIC ANTIGEN-BINDING POLYPEPTIDES

(71) Applicant: X-BODY, Inc., Waltham, MA (US)

(72) Inventors: Yan Chen, Lexington, MA (US); Richard W. Wagner, Cambridge, MA (US); Keming Zhang, Waltham, MA (US); Pascale Richalet, Waltham, MA (US)

(73) Assignee: X-BODY, Inc., Waltham, MA (US)

( * ) Notice: Subject to any disclaimer, the term of this patent is extended or adjusted under 35 U.S.C. 154(b) by 24 days.

(21) Appl. No.: 14/664,018

(22) Filed: Mar. 20, 2015

(65) Prior Publication Data

US 2015/0299335 A1    Oct. 22, 2015

Related U.S. Application Data

(60) Provisional application No. 61/968,437, filed on Mar. 21, 2014.

(51) Int. Cl.
| | |
|---|---|
| *A61K 39/00* | (2006.01) |
| *C07K 16/00* | (2006.01) |
| *C07K 16/28* | (2006.01) |
| *C07K 16/32* | (2006.01) |
| *C07K 16/30* | (2006.01) |
| *C07K 16/46* | (2006.01) |
| *A61K 38/00* | (2006.01) |

(52) U.S. Cl.
CPC .......... *C07K 16/32* (2013.01); *C07K 16/2863* (2013.01); *C07K 16/30* (2013.01); *C07K 16/46* (2013.01); *A61K 38/00* (2013.01); *C07K 2317/31* (2013.01); *C07K 2317/56* (2013.01); *C07K 2317/565* (2013.01); *C07K 2317/622* (2013.01); *C07K 2317/64* (2013.01); *C07K 2317/92* (2013.01)

(58) Field of Classification Search
None
See application file for complete search history.

(56) References Cited

U.S. PATENT DOCUMENTS

| 5,942,602 A * | 8/1999 | Wels ................ A61K 47/48561 |
| | | 424/1.49 |
| 2006/0263367 A1 | 11/2006 | Fey et al. |
| 2012/0121597 A1* | 5/2012 | Ho ...................... C07K 16/1063 |
| | | 424/136.1 |
| 2014/0193402 A1* | 7/2014 | Wiegand .......... A61K 39/39541 |
| | | 424/133.1 |
| 2014/0302039 A1* | 10/2014 | Jeong ..................... C07K 16/22 |
| | | 424/138.1 |

FOREIGN PATENT DOCUMENTS

| WO | 2011/130580 A1 | 10/2011 |
| WO | 2012/025530 A1 | 3/2012 |
| WO | 2012/125733 A2 | 9/2012 |
| WO | 2012/143524 A2 | 10/2012 |
| WO | 2013/033008 A2 | 3/2013 |

OTHER PUBLICATIONS

Vaneycken et al. (The FASEB Journal, 2011, 25:2433-2446).*
Harmsen et al., Applied Microbiology and Biotechnology, 2007, 77:13-22.*
Rudikoff et al. (Proceedings of the National Academy of Sciences, 1982, 79:1979-1983.*
MacCallum et al. (Journal of Molecular Biology, 1996, 262:732-745.*
De Pascalis et al. (Journal of Immunology, 2002, 169:3076-3084).*
Casset et al. (Biochemical and Biophysical Research Communications, 2003, 307:198-205).*
Vajdos et al. (Journal of Molecular Biology, 2002, 320:415-428).*
Holm et al. (Molecular Immunology, 2007:1075-1084).*
Chen et al. (Journal of Molecular Biology, 1999, 293:865-881).*
Padlan (Advances in Protein Chemistry, 1996, 49:57-133).*
Berglund (Berglund et al, 2008, Protein Science, 17:606-613).*
Ward et al. (Nature, 1989, 341:544-546).*
Barthelemy et al. (Journal of Biological Chemistry, 2008, 283:3639-3654).*
Yan Chen et al., (Dec. 2-6, 2012). Selection of human-derived antibodies targeting HER2 expressed on live cells with dsDNA display and massively parallel deep sequencing analysis. Poster session presented at the Annual Meeting of The Antibody Society, San Diego, CA.
Laventie et al. (2011) "Heavy chain-only antibodies and tetravalent bispecific antibody neutralizing *Staphylococcus aureus* leukotoxins," Proc. Natl. Acad. Sci. USA. 108(39):16404-16409.
International Search Report with Written Opinion corresponding to International Patent Application No. PCT/US2015/021668, dated May 26, 2015.
Olaussen et al. (2009) "Synergistic proapoptotic effects of the two tyrosine kinase inhibitors pazopanib and lapatinib on multiple carcinoma cell lines," Oncogene. 28(48):4249-4260.

\* cited by examiner

*Primary Examiner* — Julie Wu
(74) *Attorney, Agent, or Firm* — Lathrop Gage LLP; James H. Velema, Esq.

(57) ABSTRACT

The present invention provides antigen-binding polypeptides (e.g., bi-specific antigen-binding polypeptides) that specifically bind to a first and a second target antigen with high affinity. The present invention also provides novel antigen-binding polypeptides that specifically bind to HER2 and antagonize HER2 activation. The invention also provides nucleic acids encoding the antigen-binding polypeptides, recombinant expression vectors and host cells for making such antigen binding polypeptides. Methods of using antigen-binding polypeptide of the invention to treat disease (e.g., cancer) are also encompassed by the invention.

9 Claims, 12 Drawing Sheets
Specification includes a Sequence Listing.

SEQUENCE LISTING

<160> NUMBER OF SEQ ID NOS: 32

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Trp Ala Arg Gly Ser Thr Ser Pro His Gly Leu Asp Val
1               5                   10

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Met Gly Trp Met Asn Pro Lys Ser Gly Gly Thr Tyr Tyr Ala Gln
1               5                   10                  15

Lys Phe Gln Gly
            20

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Asn Tyr Met His
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Pro Arg Ala Ala Thr Phe Asp Tyr
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Asn Pro Asn Ser Gly Gly Thr Tyr Tyr Ala Gln Lys Leu Gln
1               5                   10                  15

Gly

<210> SEQ ID NO 6

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Tyr Tyr Met His
1               5

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Gly Gly Ser Gly Ser Tyr Leu Phe Asp Tyr
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ile Asn Trp Asn Gly Gly Ser Thr Gly Tyr Ala Asp Ser Val Lys
1               5                   10                  15

Gly

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Tyr Gly Met Ser
1               5

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Gly Gly Asn Gly Ser Tyr Thr Thr Pro Leu
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 11

Gly Ile Asn Trp Asn Gly Gly Ser Thr Gly Tyr Ala Asp Ser Val Lys
1               5                   10                  15

Gly

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Tyr Gly Met Ser
1               5

<210> SEQ ID NO 13
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Ala Glu Val Lys Glu Pro Gly Ala
1               5                   10                  15

Ser Val Lys Val Ser Cys Lys Ser Ser Gly Tyr Ser Phe Thr Gly Asn
            20                  25                  30

Tyr Met His Trp Val Arg Gln Ala Pro Gly Gln Gly Leu Glu Trp Met
        35                  40                  45

Gly Trp Met Asn Pro Lys Ser Gly Gly Thr Tyr Tyr Ala Gln Lys Phe
    50                  55                  60

Gln Gly Arg Val Thr Met Thr Trp Asp Thr Ser Ile Ser Thr Ala Tyr
65                  70                  75                  80

Met Glu Leu Ser Gly Leu Thr Ser Asp Asp Thr Ala Val Tyr Tyr Cys
                85                  90                  95

Ala Arg Trp Ala Arg Gly Ser Thr Ser Pro His Gly Leu Asp Val Trp
            100                 105                 110

Gly Gln Gly Thr Leu Val Thr Val Ser Ser
        115                 120

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Tyr Tyr Ala Gln Lys Leu
    50                  55                  60
```

```
Gln Gly Arg Val Thr Met Thr Thr Asp Thr Ser Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Pro Arg Ala Ala Thr Phe Asp Tyr Trp Gly Gln Gly Thr
            100                 105                 110

Leu Val Thr Val Ser Ser
        115
```

<210> SEQ ID NO 15
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gln Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Ala Arg Gly Tyr Gly Gly Ser Gly Ser Tyr Leu Phe Asp Tyr Trp Gly
            100                 105                 110

Gln Gly Thr Leu Val Thr Val Ser Ser
        115                 120
```

<210> SEQ ID NO 16
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Gln Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Phe Leu Tyr
 65                  70                  75                  80

Leu Gln Met Asn Ser Leu Arg Ala Glu Asp Thr Ala Leu Tyr His Cys
                 85                  90                  95

Ala Arg Gly Phe Gly Gly Asn Gly Ser Tyr Thr Thr Pro Leu Arg Gly
            100                 105                 110
```

Gln Gly Thr Met Val Thr Val Ser Ser
        115                 120

<210> SEQ ID NO 17
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Glu Thr Asp Thr Leu Leu Leu Trp Val Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Ser Ser Val Arg Val Ser Cys Lys Ala Ser Gly Gly Thr
        35                  40                  45

Phe Ser Arg His Ala Ile Ser Trp Val Arg Gln Ala Pro Gly Gln Gly
    50                  55                  60

Leu Glu Trp Ile Gly Gly Ile Leu Pro Ile Leu Lys Thr Pro Asn Tyr
65                  70                  75                  80

Ala Gln Arg Phe Gln Gly Arg Val Thr Ile Asn Ala Asp Glu Ser Thr
                85                  90                  95

Ser Thr Val Tyr Met Glu Met Ser Ser Leu Arg Ser Glu Asp Thr Ala
            100                 105                 110

Val Tyr Tyr Cys Ala Thr His Gly Gly Asp Arg Ser Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys Gly Gly Gly Gly Ser Gly Gly Gly Gly Ser Gly Gly Gly Gly
465                 470                 475                 480

Ser Gly Gly Gly Gly Ser Glu Val Gln Leu Val Glu Ser Gly Ala Glu
                485                 490                 495

Val Lys Glu Pro Gly Ala Ser Val Lys Val Ser Cys Lys Ser Ser Gly
            500                 505                 510

Tyr Ser Phe Thr Gly Asn Tyr Met His Trp Val Arg Gln Ala Pro Gly
    515                 520                 525

Gln Gly Leu Glu Trp Met Gly Trp Met Asn Pro Lys Ser Gly Gly Thr
    530                 535                 540

Tyr Tyr Ala Gln Lys Phe Gln Gly Arg Val Thr Met Thr Trp Asp Thr
545                 550                 555                 560

Ser Ile Ser Thr Ala Tyr Met Glu Leu Ser Gly Leu Thr Ser Asp Asp
            565                 570                 575

Thr Ala Val Tyr Tyr Cys Ala Arg Trp Ala Arg Gly Ser Thr Ser Pro
            580                 585                 590

His Gly Leu Asp Val Trp Gly Gln Gly Thr Leu Val Thr Val Ser Ser
            595                 600                 605

<210> SEQ ID NO 18
<211> LENGTH: 588
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Arg His
            20                  25                  30

Ala Ile Ser Trp Val Arg Gln Ala Pro Gly Gln Gly Leu Glu Trp Ile
        35                  40                  45

Gly Gly Ile Leu Pro Ile Leu Lys Thr Pro Asn Tyr Ala Gln Arg Phe
    50                  55                  60

Gln Gly Arg Val Thr Ile Asn Ala Asp Glu Ser Thr Ser Thr Val Tyr
65                  70                  75                  80

Met Glu Met Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val

```
            100                 105                 110
Thr Val Ser Ser Ala Ser Thr Lys Gly Pro Ser Val Phe Pro Leu Ala
            115                 120                 125
Pro Ser Ser Lys Ser Thr Ser Gly Gly Thr Ala Ala Leu Gly Cys Leu
            130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                    165                 170                 175
Gly Leu Tyr Ser Leu Ser Ser Val Val Thr Val Pro Ser Ser Ser Leu
                    180                 185                 190
Gly Thr Gln Thr Tyr Ile Cys Asn Val Asn His Lys Pro Ser Asn Thr
            195                 200                 205
Lys Val Asp Lys Arg Val Glu Pro Lys Ser Cys Asp Lys Thr His Thr
210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
            245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
            325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                    405                 410                 415
Gln Gln Gly Asn Val Phe Ser Cys Ser Val Met His Glu Ala Leu His
                    420                 425                 430
Asn His Tyr Thr Gln Lys Ser Leu Ser Leu Ser Pro Gly Lys Gly Gly
            435                 440                 445
Gly Gly Ser Gly Gly Gly Gly Ser Gly Gly Gly Gly Ser Gly Gly Gly
            450                 455                 460
Gly Ser Glu Val Gln Leu Val Glu Ser Gly Ala Glu Val Lys Glu Pro
465                 470                 475                 480
Gly Ala Ser Val Lys Val Ser Cys Lys Ser Ser Gly Tyr Ser Phe Thr
                    485                 490                 495
Gly Asn Tyr Met His Trp Val Arg Gln Ala Pro Gly Gln Gly Leu Glu
            500                 505                 510
Trp Met Gly Trp Met Asn Pro Lys Ser Gly Gly Thr Tyr Tyr Ala Gln
            515                 520                 525
```

```
Lys Phe Gln Gly Arg Val Thr Met Thr Trp Asp Thr Ser Ile Ser Thr
            530                 535                 540

Ala Tyr Met Glu Leu Ser Gly Leu Thr Ser Asp Asp Thr Ala Val Tyr
545                 550                 555                 560

Tyr Cys Ala Arg Trp Ala Arg Gly Ser Thr Ser Pro His Gly Leu Asp
                565                 570                 575

Val Trp Gly Gln Gly Thr Leu Val Thr Val Ser Ser
            580                 585

<210> SEQ ID NO 19
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Ala Glu Val Lys
            20                  25                  30

Glu Pro Gly Ala Ser Val Lys Val Ser Cys Lys Ser Ser Gly Tyr Ser
        35                  40                  45

Phe Thr Gly Asn Tyr Met His Trp Val Arg Gln Ala Pro Gly Gln Gly
    50                  55                  60

Leu Glu Trp Met Gly Trp Met Asn Pro Lys Ser Gly Gly Thr Tyr Tyr
65                  70                  75                  80

Ala Gln Lys Phe Gln Gly Arg Val Thr Met Thr Trp Asp Thr Ser Ile
                85                  90                  95

Ser Thr Ala Tyr Met Glu Leu Ser Gly Leu Thr Ser Asp Asp Thr Ala
            100                 105                 110

Val Tyr Tyr Cys Ala Arg Trp Ala Arg Gly Ser Thr Ser Pro His Gly
        115                 120                 125

Leu Asp Val Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
```

```
                      290                 295                 300
Asp Gly Val Glu Val His Asn Ala Lys Thr Lys Pro Arg Glu Glu Gln
305                 310                 315                 320

Tyr Asn Ser Thr Tyr Arg Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460

Ser Leu Ser Leu Ser Pro Gly Lys Gly Gly Gly Ser Gly Gly Gly
465                 470                 475                 480

Gly Ser Gly Gly Gly Ser Gly Gly Gly Ser Gln Val Gln Leu
                485                 490                 495

Val Gln Ser Gly Ala Glu Val Lys Lys Pro Gly Ser Ser Val Arg Val
                500                 505                 510

Ser Cys Lys Ala Ser Gly Gly Thr Phe Ser Arg His Ala Ile Ser Trp
                515                 520                 525

Val Arg Gln Ala Pro Gly Gln Gly Leu Glu Trp Ile Gly Gly Ile Leu
                530                 535                 540

Pro Ile Leu Lys Thr Pro Asn Tyr Ala Gln Arg Phe Gln Gly Arg Val
545                 550                 555                 560

Thr Ile Asn Ala Asp Glu Ser Thr Ser Thr Val Tyr Met Glu Met Ser
                565                 570                 575

Ser Leu Arg Ser Glu Asp Thr Ala Val Tyr Tyr Cys Ala Thr His Gly
                580                 585                 590

Gly Asp Arg Ser Tyr Trp Gly Gln Gly Thr Leu Val Thr Val Ser Ser
                595                 600                 605

<210> SEQ ID NO 20
<211> LENGTH: 588
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Ala Glu Val Lys Glu Pro Gly Ala
1               5                   10                  15

Ser Val Lys Val Ser Cys Lys Ser Ser Gly Tyr Ser Phe Thr Gly Asn
                20                  25                  30

Tyr Met His Trp Val Arg Gln Ala Pro Gly Gln Gly Leu Glu Trp Met
                35                  40                  45
```

```
Gly Trp Met Asn Pro Lys Ser Gly Gly Thr Tyr Tyr Ala Gln Lys Phe
     50                  55                  60
Gln Gly Arg Val Thr Met Thr Trp Asp Thr Ser Ile Ser Thr Ala Tyr
 65                  70                  75                  80
Met Glu Leu Ser Gly Leu Thr Ser Asp Asp Thr Ala Val Tyr Tyr Cys
                 85                  90                  95
Ala Arg Trp Ala Arg Gly Ser Thr Ser Pro His Gly Leu Asp Val Trp
             100                 105                 110
Gly Gln Gly Thr Leu Val Thr Val Ser Ser Ala Ser Thr Lys Gly Pro
         115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Arg Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys Gly Gly Gly Ser Gly Gly Gly Ser Gly Gly
    450                 455                 460
Gly Gly Ser Gly Gly Gly Gly Ser Gln Val Gln Leu Val Gln Ser Gly
```

```
            465                 470                 475                 480
Ala Glu Val Lys Lys Pro Gly Ser Ser Val Arg Val Ser Cys Lys Ala
                    485                 490                 495

Ser Gly Gly Thr Phe Ser Arg His Ala Ile Ser Trp Val Arg Gln Ala
                500                 505                 510

Pro Gly Gln Gly Leu Glu Trp Ile Gly Gly Ile Leu Pro Ile Leu Lys
            515                 520                 525

Thr Pro Asn Tyr Ala Gln Arg Phe Gln Gly Arg Val Thr Ile Asn Ala
        530                 535                 540

Asp Glu Ser Thr Ser Thr Val Tyr Met Glu Met Ser Ser Leu Arg Ser
545                 550                 555                 560

Glu Asp Thr Ala Val Tyr Tyr Cys Ala Thr His Gly Gly Asp Arg Ser
                565                 570                 575

Tyr Trp Gly Gln Gly Thr Leu Val Thr Val Ser Ser
            580                 585

<210> SEQ ID NO 21
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Ser Ser Leu Ser
                20                  25                  30

Ala Ser Val Gly Asp Arg Val Thr Ile Thr Cys Gln Ala Ser Gln Asp
            35                  40                  45

Ile Ser Asn Trp Leu Asn Trp Tyr Gln Gln Lys Pro Gly Lys Ala Pro
        50                  55                  60

Lys Leu Leu Ile Tyr Glu Ala Ser Asn Leu Glu Thr Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Tyr Cys Gln Gln Tyr Asn
                100                 105                 110

Asn Val Leu Arg Thr Phe Gly Gln Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 22
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Val Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Trp
            20                  25                  30

Leu Asn Trp Tyr Gln Gln Lys Pro Gly Lys Ala Pro Lys Leu Leu Ile
        35                  40                  45

Tyr Glu Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Asn Val Leu Arg
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Gly Ser Gly Gly Gly Gly Ser Gly Gly Gly Gly Ser Gly
1               5                   10                  15

Gly Gly Gly Ser
            20

<210> SEQ ID NO 24
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 24

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Arg His
            20                  25                  30

Ala Ile Ser Trp Val Arg Gln Ala Pro Gly Gln Gly Leu Glu Trp Ile
        35                  40                  45

Gly Gly Ile Leu Pro Ile Leu Lys Thr Pro Asn Tyr Ala Gln Arg Phe
    50                  55                  60

Gln Gly Arg Val Thr Ile Asn Ala Asp Glu Ser Thr Ser Thr Val Tyr
65                  70                  75                  80

Met Glu Met Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

His Gly Gly Asp Arg Ser Tyr
1               5

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ile Leu Pro Ile Leu Lys Thr Pro Asn Tyr Ala Gln Arg Phe Gln
1               5                   10                  15

Gly

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg His Ala Ile Ser
1               5

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 28

Asp Val Val Met Thr Gln Ser Pro Ser Leu Ser Ala Ser Val Gly
1               5                   10                  15

Asp Arg Val Thr Ile Thr Cys Gln Ala Ser Gln Asp Ile Ser Asn Trp
            20                  25                  30

Leu Asn Trp Tyr Gln Gln Lys Pro Gly Lys Ala Pro Lys Leu Leu Ile
        35                  40                  45

Tyr Glu Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Asn Val Leu Arg
                85                  90                  95

Thr Phe Gly Gln Gly Thr Lys Val Glu Ile Lys
            100                 105

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gln Tyr Asn Asn Val Leu Arg Thr
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Ala Ser Asn Leu Glu Thr
1               5

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Ala Ser Gln Asp Ile Ser Asn Trp Leu Asn
1               5                   10

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 32

His His His His His His
1               5

BI-SPECIFIC ANTIGEN-BINDING POLYPEPTIDES

RELATED APPLICATIONS

This application claims the benefit of priority of U.S. Provisional Application No. 61/968,437, filed Mar. 21, 2014. The contents of the aforementioned application are hereby incorporated by reference in its entirety.

BACKGROUND

Bi-specific antigen binding polypeptides, such as antibodies and antibody-like molecules, hold great promise as therapeutics due their ability to target multiple antigens simultaneously. However, manufacturing of these molecules is a challenge. In the case of bi-specific antibodies, mis-pairing in both heavy and light chains often occurs during production, which reduces the yield of the bi-specific antibodies and makes purification challenging.

To overcome the problems associated with manufacturing of bi-specific antibodies, complex engineering in the antibody constant or variable regions has been attempted. For example, bi-specific antibodies have been generated in which the VH and VL of the individual antibodies are genetically fused via a linker (see e.g., US2010/0254989A1). In another approach individual antibodies were produced with mutations in the Fc in residues of the human IgG4 responsible for Fab exchange (see e.g., Van der Neut at al., Science (2007) 317: 1554). In yet another approach, mouse quadromas were employed for generating bi-specific antibodies. In this approach, the mouse and rat antibodies predominantly form the original VH/VL pairings and the bi-specific antibody consists of the rat and mouse Fc (see e.g., Lindhofer et al., J Immunol. (1995) 155: 1246-1252). Finally, bi-specific antibodies have been generated that use a single, common light chain that does not contribute to antigen binding (see e.g., Merchant et al., Nature Biotechnology (1998) 16: 677-681). However, in spite of these extensive antibody engineering efforts, bi-specific antibodies continue to suffer from poor stability and low functional expression yields.

Accordingly, there is a need in the art for novel antigen-binding polypeptides that are highly expressed and easily purified.

SUMMARY OF THE INVENTION

The present invention provides bi-specific antigen-binding polypeptides that are highly expressed, easily purified, highly stable and have a high affinity for their target antigens. In certain embodiments, the bi-specific antigen-binding polypeptides bind to both PDGFRβ and HER2 with high affinity and antagonize both PDGFRβ and HER2 activity. In certain embodiments, the bi-specific antigen-binding polypeptides bind to both PDGFRβ and VEGF with high affinity and antagonize both PDGFRβ and VEGF activity. The present invention also provides novel antigen-binding polypeptides (e.g., VH domains) that specifically bind to HER2 and antagonize HER2 activation. Such antigen-binding polypeptides are particularly useful for treating cancer. The invention also provides nucleic acids encoding the antigen-binding polypeptides, recombinant expression vectors and host cells for making such antigen-binding polypeptides. Methods of using the antigen-binding polypeptides of the invention to treat disease (e.g., cancer) are also encompassed by the invention.

Accordingly, in one aspect the invention provides an isolated bi-specific antigen-binding polypeptide comprising an antibody heavy chain comprising a first VH domain that specifically binds to first antigen, C-terminally linked to a second VH domain that specifically binds to a second antigen, wherein the polypeptide is devoid of antibody light chains.

In certain embodiments, the antibody heavy chain is genetically linked to the second VH domain through an amino acid linker. In one particular embodiment, the linker comprises the amino acid sequence set forth in SEQ ID No: 23.

In certain embodiments, the antigen-binding polypeptide further comprises an antibody light chain, the light chain comprising a VL domain that specifically binds to an antigen, wherein the heavy and light chains are naturally paired. In one particular embodiment, the VL domain binds to the first antigen. In one particular embodiment, the VL domain binds to a third antigen. In one particular embodiment, the first and third antigens are in different regions of the same molecule. In one particular embodiment, the first and third antigens are on different molecule.

In certain embodiments, the invention provides an antigen-binding polypeptide comprising a dimer of two antigen-binding polypeptides disclosed herein, the two antigen-binding polypeptides naturally dimerized through the heavy chain constant regions. In certain embodiments, the first and second antigens are different. In one particular embodiment, the first and second antigens are in different regions of the same molecule. In one particular embodiment, the first and second antigens are on different molecule.

In certain embodiments, the first antigen is human PDGFRβ or HER2. In certain embodiments, the second antigen is human PDGFRβ or HER2.

In certain embodiments, the antigen-binding polypeptide comprises a VH domain that binds specifically to human HER2 and comprises a HCDR3 comprising an amino acid sequence selected from the group consisting of SEQ ID NOs: 1, 4, 7, and 10. In certain embodiments, the VH domain further comprises a HCDR2 comprising an amino acid sequence selected from the group consisting of SEQ ID NOs: 2, 5, 8, or 11. In certain embodiments, the VH domain further comprises a HCDR1 comprising an amino acid sequence selected from the group consisting of SEQ ID NOs: 3, 6, 9, or 12. In certain embodiments, the VH domain amino acid sequence shares at least 80% amino acid sequence identity with a VH domain amino acid sequence selected from the group consisting of SEQ ID NOs: 13, 14, 15, and 16. In certain embodiments, the VH domain comprises an amino acid sequence selected from the group consisting of SEQ ID NOs: 13, 14, 15, and 16.

In certain embodiments, the antigen-binding polypeptide comprises a VH domain that binds specifically to human PDGFRβ and comprises a HCDR3 comprising the amino acid sequence set forth in SEQ ID NOs: 25. In certain embodiments, the VH domain further comprises a HCDR2 comprising the amino acid sequence set forth in SEQ ID NOs: 26. In certain embodiments, the VH domain further comprises a HCDR1 comprising the amino acid sequence set forth in SEQ ID NOs: 27. In certain embodiments, the VH domain comprises the amino acid sequence set forth in SEQ ID NOs: 24.

In certain embodiments, the antigen-binding polypeptide comprises a heavy chain comprising the amino acid sequence set forth in SEQ ID NOs: 18 or 20.

In certain embodiments, the antigen-binding polypeptide comprises a VL domain that binds specifically to human PDGFRβ and comprises a LCDR3 comprising the amino acid sequence set forth in SEQ ID NOs: 29. In certain embodiments, the VL domain further comprises a LCDR2 comprising the amino acid sequence set forth in SEQ ID NOs: 30. In certain embodiments, the VL domain further comprises a LCDR1 comprising the amino acid sequence set forth in SEQ ID NOs: 31. In certain embodiments, the VL domain comprises the amino acid sequence set forth in SEQ ID NOs: 28.

In certain embodiments, the antigen-binding polypeptide comprises an antibody light chain comprising the amino acid sequence set forth in SEQ ID NOs: 22.

In another aspect, the invention provides an isolated antigen-binding polypeptide that specifically binds to HER2, comprising the CDR3 comprising an amino acid sequence selected from the group consisting of SEQ ID NOs: 1, 4, 7, and 10.

In certain embodiments, the binding antigen-binding polypeptide comprises a VH domain comprising a CDR3 comprising an amino acid sequence selected from the group consisting of SEQ ID NOs: 1, 4, 7, and 10. In certain embodiments, the VH domain further comprises a CDR2 comprising an amino acid sequence selected from the group consisting of SEQ ID NOs: 2, 5, 8, or 11. In certain embodiments, the VH domain further comprises a CDR1 comprising an amino acid sequence selected from the group consisting of SEQ ID NOs: 3, 6, 9, or 12. In certain embodiments, the VH domain comprises an amino acid sequence sharing at least 80% amino acid sequence identity with an amino acid sequence selected from the group consisting of SEQ ID NOs: 13, 14, 15, and 16. In certain embodiments, the VH domain comprises an amino acid sequence selected from the group consisting of SEQ ID NOs: 13, 14, 15, and 16.

In another aspect, the invention provides an antigen-binding polypeptide that binds to the same epitope on HER2 as a VH domain having an amino acid sequence selected from the group consisting of SEQ ID NOs: 13, 14, 15, and 16. In certain embodiments, the antigen-binding polypeptide comprises a VH domain.

In another aspect, the invention provides an antigen-binding polypeptide that competes for binding to HER2 with a VH domain having an amino acid sequence selected from the group consisting of SEQ ID NOs: 13, 14, 15, and 16. In certain embodiments, the antigen-binding polypeptide comprises a VH domain.

In a further aspect, the invention provides an isolated nucleic acid encoding an antigen-binding polypeptide of the invention.

In a further aspect, the invention provides a recombinant expression vector comprising an isolated nucleic acid encoding an antigen-binding polypeptide of the invention.

In a further aspect, the invention provides a host cell expressing an antigen-binding polypeptide of the invention.

In a further aspect, the invention provides a method of producing an antigen-binding polypeptide of the invention, comprising culturing a host cell capable of expressing a binding polypeptide of the invention under conditions such that the antigen-binding polypeptide is produced by the host cell.

In a further aspect, the invention provides a pharmaceutical composition comprising a antigen-binding polypeptide of the invention and one or more pharmaceutically acceptable carrier.

In a further aspect, the invention provides a method for treating a disease or disorder, the method comprising administering to a subject in need of thereof a pharmaceutical composition of the invention. In certain embodiments, the disease or disorder is cancer (e.g., breast and ovarian cancer).

DETAILED DESCRIPTION

Figure 1:
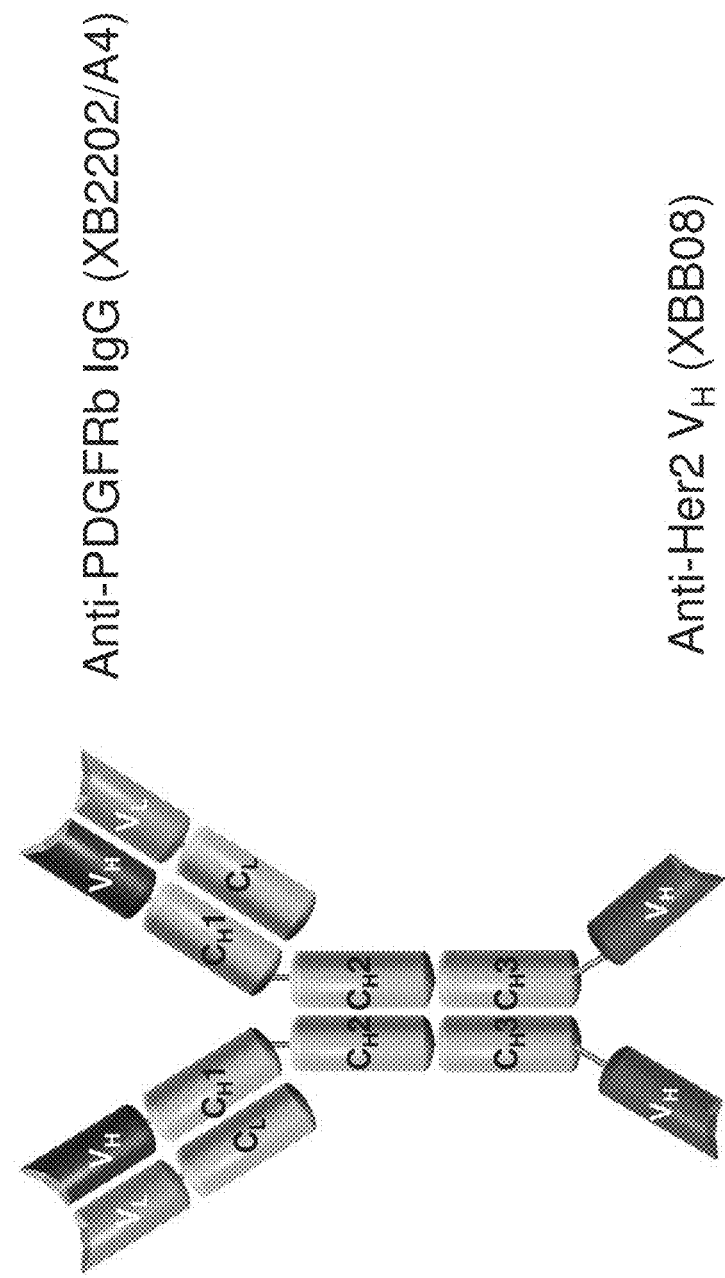
FIG. 1 is a schematic representation of an exemplary bi-specific antigen-binding polypeptide of the invention.

The present invention provides bi-specific antigen-binding polypeptides that are highly expressed, easily purified, highly stable and have a high affinity for their target antigens. In certain embodiments, the bi-specific antigen-binding polypeptides bind to both PDGFRβ and HER2 with high affinity and antagonize both PDGFRβ and HER2 activity. In certain embodiments, the bi-specific antigen-binding polypeptides bind to both PDGFRβ and VEGF with high affinity and antagonize both PDGFRβ and VEGF activity. The present invention also provides novel antigen-binding polypeptides (e.g., VH domains) that specifically bind to HER2 and antagonize HER2 activation. Such antigen-binding polypeptides are particularly useful for treating cancer. The invention also provides nucleic acids encoding the antigen-binding polypeptides, recombinant expression vectors and host cells for making such antigen-binding polypeptides. Methods of using the antigen-binding polypeptides of the invention to treat disease (e.g., cancer) are also encompassed by the invention.

I. Definitions

In order that the present invention may be more readily understood, certain terms are first defined.

As used herein, the term "PDGFRβ" refers to platelet-derived growth factor receptor beta. PDGFRβ nucleotide and polypeptide sequences are well known in the art. An exemplary human PDGFRβ amino sequence is set forth in GenBank deposit GI:4505683 and an exemplary mouse PDGFRβ amino sequence is set forth in GenBank deposit GI:226371752.

As used herein, the term "HER2" refers to the receptor tyrosine-protein kinase erbB-2. HER2 nucleotide and polypeptide sequences are well known in the art. An exemplary human HER2 amino sequence is set forth in GenBank deposit GI:54792096 and an exemplary mouse HER2 amino sequence is set forth in GenBank deposit GI:54873610.

As used herein, the term "VEGF" refers to all member of the vascular endothelial growth factor family, including the VEGF-A, VEGF-B, VEGF-C, VEGF-D, PlGF, proteins and splice variants of the same, including $VEGF_{121}$, $VEGF_{121}b$, $VEGF_{145}$, $VEGF_{165}$, $VEGF_{165}b$, $VEGF_{189}$, and $VEGF_{206}$. VEGF nucleotide and polypeptide sequences are well known in the art. An exemplary human VEGF amino sequence is set forth in GenBank deposit GI:32699990 and an exemplary mouse VEGF amino sequence is set forth in GenBank deposit GI: GI:160358815.

As used herein, the term "bi-specific antigen-binding polypeptide" refers to an antigen-binding polypeptide that can specifically bind to two or more different antigens simultaneously.

As used herein, the term "antigen" refers to the binding site or epitope recognized by an antigen-binding polypeptide.

As used herein, the term "antibody" refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated VH) and a heavy chain constant region. The heavy chain constant region comprises three domains, CH1, CH2 and CH3. Each light chain comprises a light chain variable region (abbreviated VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR).

As used herein, the term "antigen-binding portion" of an antibody includes any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding portions include: (i) Fab fragments; (ii) F(ab')₂ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies, and minibodies are also encompassed within the expression "antigen-binding portion."

As used herein, the terms "VH domain" and "VL domain" refer to single antibody variable heavy and light domains, respectively, comprising FR (Framework Regions) 1, 2, 3, and 4 and CDR (Complementary Determinant Regions) 1, 2 and 3 (see Kabat et al. (1991) Sequences of Proteins of Immunological Interest. (NIH Publication No. 91-3242, Bethesda).

As used herein, the term "naturally dimerized" refers to dimers of antigen binding polypeptides, wherein the heavy chain constant regions are associated in the same way as in a naturally-occurring, tetrameric antibody molecule.

As used herein, the term "naturally paired" refers to antibody heavy and light chain pairs that are associated through the natural heavy chain/light chain interaction interface in the same way as in a naturally-occurring, tetrameric antibody molecule.

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977). Kabat et al., Sequences of protein of immunological interest. (1991), Chothia et al., J. Mol. Biol. 196:901-917 (1987), and by MacCallum et al., J. Mol. Biol. 262:732-745 (1996) (each of which is herein incorporated by reference in its entirety) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat, based on sequence comparisons.

As used herein, the term "framework (FR) amino acid residues" refers to those amino acids in the framework region of an immunogobulin chain. The term "framework region" or "FR region" as used herein includes the amino acid residues that are part of the variable region, but are not part of the CDRs (e.g., using the Kabat definition of CDRs).

As used herein, the term "genetically linked" refers to the linkage of two or more polypeptides using recombinant DNA techniques. In certain embodiments, this involves the production of a chimeric gene encoding a fusion of the two or more polypeptides.

As used herein, the term "specifically binds to" refers to the ability of a binding polypeptide to bind to an antigen with an Kd of at least about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, or more, and/or bind to an antigen with an affinity that is at least two-fold greater than its affinity for a nonspecific antigen. It shall be understood, however, that the binding polypeptide are capable of specifically binding to two or more antigens which are related in sequence. For example, the binding polypeptides of the invention can specifically bind to both a human antigen and a non-human ortholog of that antigen.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a recombinant expression vector has been introduced. It should be understood that this term is intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "PDGFRβ-associated disease or disorder" includes disease states and/or symptoms associated with PDGFRβ activity. Exemplary PDGFRβ-associated diseases or disorders include, but are not limited to, age-related macular degeneration (AMD) and cancer.

As used herein, the term "HER2-associated disease or disorder" includes disease states and/or symptoms associated with HER2 activity. Exemplary HER2-associated diseases or disorders include, but are not limited to, cancer (e.g., breast and ovarian cancer).

As used herein, the term "VEGF-associated disease or disorder" includes disease states and/or symptoms associated with VEGF activity. Exemplary VEGF-associated diseases or disorders include, but are not limited to, conditions associated with neovascularization, e.g., age-related macular degeneration (AMD) and cancer.

As used herein, the term "treat," "treating," and "treatment" refer to therapeutic or preventative measures described herein. The methods of "treatment" employ administration of an antibody or antigen binding portion of the present invention to a subject, for example, a subject having a disease or disorder (e.g., cancer) or predisposed to having a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" refers to that amount of a binding polypeptide that is sufficient to effect treatment, prognosis or diagnosis of a disease or disorder, when administered to a subject. A therapeutically effective amount will vary depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 1 ug to about 5,000 mg, about 1 mg to about 1,000 mg, or about 10 mg to about 100 mg of a binding polypeptide according to the invention. Dosage regimens may be adjusted to provide the optimum therapeutic response. An effective amount is also one in which any toxic or detrimental effects (i.e., side effects) of a binding polypeptide are minimized and/or outweighed by the beneficial effects.

As used herein, the term "subject" includes any human or non-human animal.

II. Anti-HER2 Antigen-Binding Polypeptides

In one aspect, the invention provides antigen-binding polypeptides (e.g., bi-specific antigen binding polypeptides, antibodies, or antigen binding fragments thereof) that specifically bind to HER2 and inhibit HER2 activity. Such binding polypeptides are particularly useful for treating HER2-associated disease or disorders (e.g., cancers, such as breast and ovarian cancers).

In general, anti-HER2 antigen-binding polypeptides of the invention comprise a heavy chain CDR3 (HCDR3) amino acid sequence that specifically binds to HER2. Non-limiting HCDR3 sequences suitable for use in the binding polypeptides of the invention include the HCDR3 amino acid sequences set forth herein in SEQ ID NOs: 1, 4, 7, or 10. In other embodiments, the HCDR3 sequence is a variant of SEQ ID NOs: 1, 4, 7, or 10 which comprises at least one (e.g., one, two, three, etc.) conservative amino acid substitutions relative to SEQ ID NO: 1, 4, 7, or 10.

Any polypeptide that can incorporate the HER2-binding HCDR3 sequences disclosed herein can be used to produce the antigen-binding polypeptides of the invention including without limitation antibodies or fragments thereof (e.g., VH domains) and immunoglobulin-like domains. Suitable immunoglobulin-like domains include, without limitation, fibronectin domains (see, for example, Koide et al. (2007), *Methods Mol. Biol.* 352: 95-109, which is incorporated by reference herein in its entirety), DARPin (see, for example, Stumpp et al. (2008) *Drug Discov. Today* 13 (15-16): 695-701, which is incorporated by reference herein in its entirety), Z domains of protein A (see, Nygren et al. (2008) *FEBS J.* 275 (11): 2668-76, which is incorporated by reference herein in its entirety), Lipocalins (see, for example, Skerra et al. (2008) *FEBS J.* 275 (11): 2677-83, which is incorporated by reference herein in its entirety), Affilins (see, for example, Ebersbach et al. (2007) *J. Mol. Biol.* 372 (1): 172-85, which is incorporated by reference herein in its entirety), Affitins (see, for example, Krehenbrink et al. (2008). *J. Mol. Biol.* 383 (5): 1058-68, which is incorporated by reference herein in its entirety), Avimers (see, for example, Silverman et al. (2005) *Nat. Biotechnol.* 23 (12): 1556-61, which is incorporated by reference herein in its entirety), Fynomers (see, for example, Grabulovski et al. (2007) *J Biol Chem* 282 (5): 3196-3204, which is incorporated by reference herein in its entirety), and Kunitz domain peptides (see, for example, Nixon et al. (2006) *Curr Opin Drug Discov Devel* 9 (2): 261-8, which is incorporated by reference herein in its entirety).

In certain embodiments, the anti-HER2 antigen-binding polypeptides comprise antibodies or antibody fragments comprising a VH domain. Exemplary CDR and VH domain amino acid sequences suitable for use in the invention are set forth in Table 1 and 2 herein.

TABLE 1

CDR amino acid sequences of exemplary anti-HER2 VH domains.

| Clone name | CDR3 | SEQ ID NO. | CDR2 | SEQ ID NO. | CDR1 | SEQ ID NO. |
|---|---|---|---|---|---|---|
| B8 | WARGSTSPHGLDV | 1 | WMGWMNPKSGGTYYAQKFQG | 2 | GNYMH | 3 |
| B12 | DPRAATFDY | 4 | WINPNSGGTYYAQKLQG | 5 | GYYMH | 6 |

TABLE 1-continued

CDR amino acid sequences of exemplary anti-HER2 VH domains.

| Clone name | CDR3 | SEQ ID NO. | CDR2 | SEQ ID NO. | CDR1 | SEQ ID NO. |
|---|---|---|---|---|---|---|
| E5 | GYGGSGSYLFDY | 7 | GINWNGGSTGYADSVKG | 8 | DYGMS | 9 |
| H6 | GFGGNGSYTTPL | 10 | GINWNGGSTGYADSVKG | 11 | DYGMS | 12 |

TABLE 2

Amino acid sequences of exemplary anti-HER2 VH domains.

| Clone name | VH Amino Acid Sequence | SEQ ID NO. |
|---|---|---|
| B8 | EVQLVESGAEVKEPGASVKVSCKSSGYSFTGNYMHWVRQAPGQGLEWMGWMNPKS GGTYYAQKFQGRVTMTWDTSISTAYMELSGLTSDDTAVYYCARWARGSTSPHGLD VWGQGTLVTVSS | 13 |
| B12 | QVQLVQSGAEVKKPGASVKVSCKASGYTFTGYYMHWVRQAPGQGLEWMGWINPNS GGTYYAQKLQGRVTMTTDTSTSTAYMELRSLRSDDTAVYYCARDPRAATFDYWGQ GTLVTVSS | 14 |
| E5 | QVQLVESGGGVVRPGGSLRLSCAASGFTFDDYGMSWVRQAPGKGLEWVSGINWNG GSTGYADSVKGRFTISRDNAKNSLYLQMNSLRAEDTALYHCARGYGGSGSYLFDY WGQGTLVTVSS | 15 |
| H6 | QVQLVESGGGVVRPGGSLRLSCAASGFTFDDYGMSWVRQAPGKGLEWVSGINWNG GSTGYADSVKGRFTISRDNAKNFLYLQMNSLRAEDTALYHCARGFGGNGSYTTPL RGQGTMVTVSS | 16 |

In certain embodiments, the anti-HER2 VH domain comprises the HCDR3 amino acid sequence set forth in SEQ ID NO:1, 4, 7, or 10, together with a HCDR2 and/or a HCDR1 sequence independently selected from any one of the heavy chain HCDR2 or HCDR1 amino acid sequences set forth in Table 1.

In certain embodiments, the anti-HER2 antigen-binding polypeptides comprise HCDR3, HCDR2 and HCDR1 amino acid sequences selected from the group consisting of SEQ ID NO: 1, 2 and 3; 4, 5 and 6; 7, 8 and 9; and 10, 11 and 12, respectively.

In certain embodiments, the anti-HER2 antigen-binding polypeptides comprises at least one of the VH amino acid sequences set forth in SEQ ID NO: 13, 14, 15, or 16.

In certain embodiments, the anti-HER2 antigen-binding polypeptides comprise one or more CDR amino acid sequences selected from the group consisting of SEQ ID NO: 1-12, wherein the one or more CDR region amino acid sequences comprise at least one or more conservative amino acid substitutions (e.g., 1, 2, 3, 4, or 5 conservative amino acid substitutions). Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in an anti-PDGFRβ antibody is preferably replaced with another amino acid residue from the same class. Methods of identifying amino acid conservative substitutions which do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:412-417 (1997), each of which is incorporated by reference herein in its entirety).

In certain embodiment, the present invention provides anti-HER2 antigen-binding polypeptides that comprise a VH and/or VL region amino acid sequence with about 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the VH region amino acid sequence set forth in SEQ ID NO: 13, 14, 15, or 16.

In certain embodiments, the anti-HER2 antigen-binding polypeptides bind to HER2 with a Kd of 1.2 nM. In certain embodiments, the anti-HER2 antigen-binding polypeptides bind to HER2 with an on-rate of $1.39 \times 10^5$ $M^{-1}s^{-1}$. In certain embodiments, the anti-HER2 antigen-binding polypeptides bind to HER2 with an off-rate of $1.67 \times 10^4$ $s^{-1}$. In certain embodiments, the anti-HER2 antigen-binding polypeptides bind to HER2 with a Kd of 0.87 nM when formatted as a scFv molecule.

In certain embodiments, the anti-HER2 antigen-binding polypeptides bind to a different epitope on HER2 than trastuzumab (CAS#180288-69-1) and/or pertuzumab (CAS#380610-27-5). In certain embodiments, the anti-HER2 antigen-binding polypeptides bind to the same epitope on HER2 as trastuzumab and/or pertuzumab. In certain embodiments, the anti-HER2 antigen-binding polypeptides compete for binding to HER2 with trastuzumab and/or pertuzumab.

In certain embodiments, the anti-HER2 antigen-binding polypeptides disclosed herein are internalized upon binding to HER2. In one particular embodiment, the internalizing anti-HER2 antigen-binding polypeptide is linked to a cytoxic moiety (e.g., an anti-cancer agent). Suitable non-limiting cytoxic moieties are disclosed herein.

In another aspect, the present invention provides anti-HER2 antigen-binding polypeptides that bind to the same epitope on HER2 and/or cross compete with an antigen-binding polypeptide comprising the VH domain amino acid sequence set forth in SEQ ID NO: 13, 14, 15, or 16. Such antibodies can be identified using routine competition binding assays including, for example, surface plasmon resonance (SPR)-based competition assays.

III. Bi-specific Antigen-Binding Polypeptides

In another aspect, the present invention provides bi-specific antigen-binding polypeptides that specifically bind to a first and a second target antigen. Any two antigens can be targeted using the bi-specific antigen-binding polypeptides of the invention. In general, the bi-specific antigen-binding polypeptides of the invention comprise an antibody heavy chain, the heavy chain comprising a first VH domain that specifically binds to first antigen, wherein the heavy chain is linked to a second VH domain that specifically binds to a second antigen.

The antibody heavy chain can be linked to the second VH domain using art recognized means (chemical and/or genetic). In certain embodiments, the antibody heavy chain and the second VH domain are genetically linked. In one embodiment, the C-terminal amino acid of the antibody heavy chain is linked to the N-terminal amino acid of the second VH domain. This linkage can either be direct or through a linker. In one embodiment, the antibody heavy chain is linked to the N-terminal amino acid of the second VH domain through an amino acid linker comprising the sequence set forth in SEQ ID No: 23.

Figure 2:
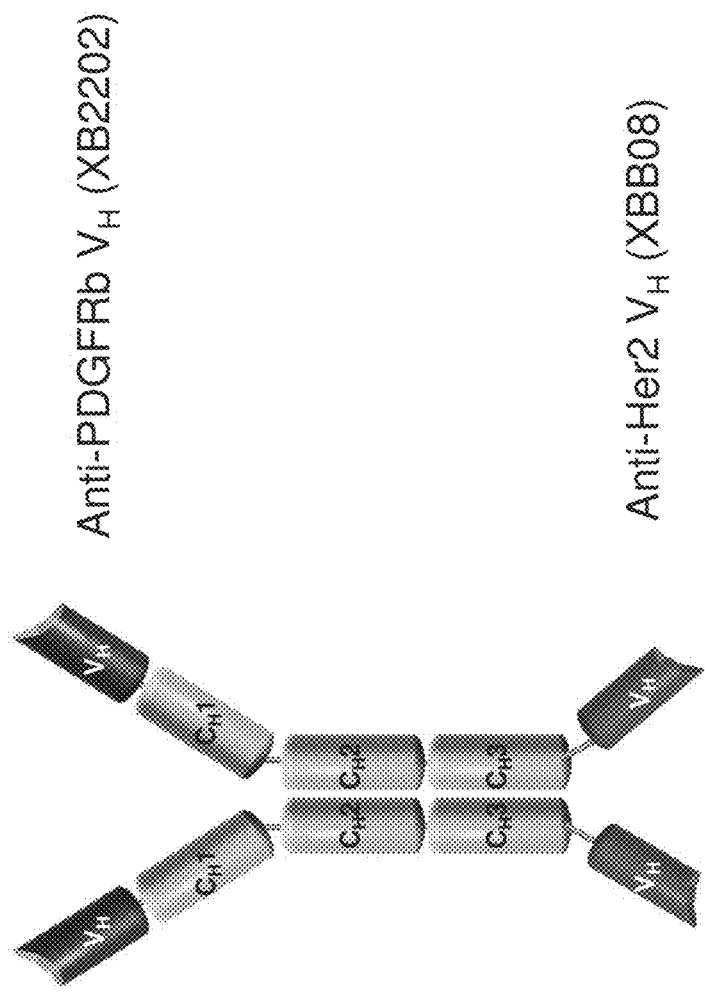
FIG. 2 is a schematic representation of an exemplary bi-specific antigen-binding polypeptide of the invention.
Figure 3:
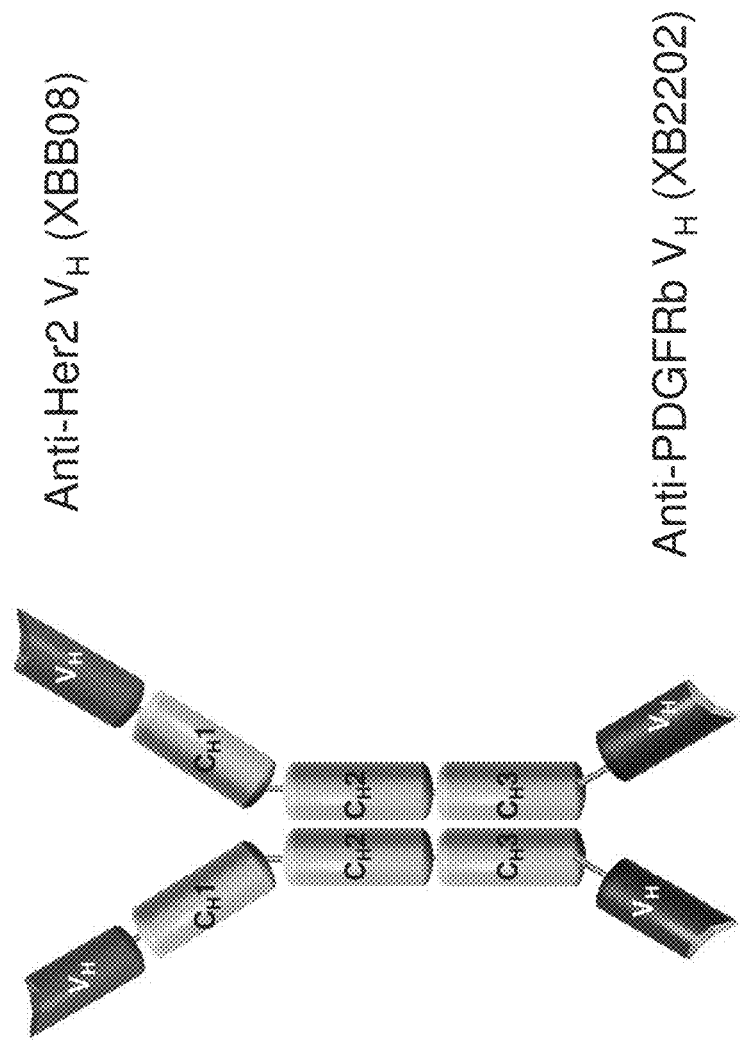
FIG. 3 is a schematic representation of an exemplary bi-specific antigen-binding polypeptide of the invention.

In certain embodiments, the bi-specific antigen-binding polypeptides are dimers of two antibody heavy chains, each antibody heavy chain comprising a first VH domain that specifically binds to first antigen, and wherein each antibody heavy chain is linked to a second VH domain that specifically binds to a second antigen. The two antibody heavy chains in the dimer are associated thought the natural heavy chain dimer interface in the same way asthis association occurs in a naturally-occurring, tetrameric antibody molecule. Exemplary bi-specific antigen-binding polypeptides having this structure are depicted in FIGS. 2 and 3 herein.

Figure 4:
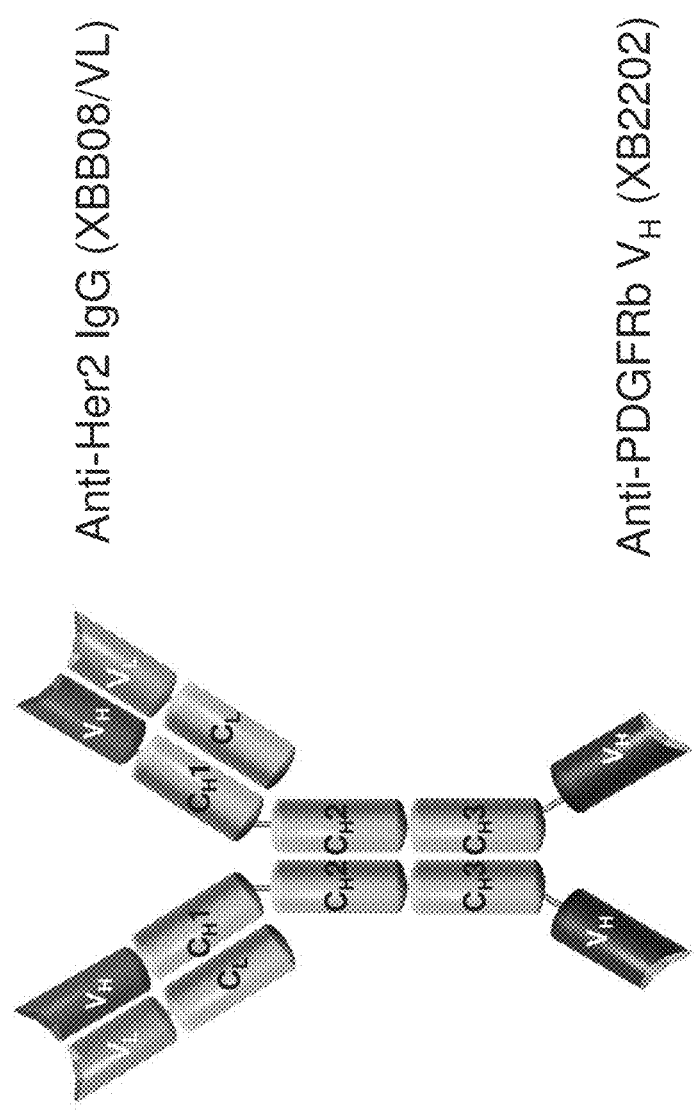
FIG. 4 is a schematic representation of an exemplary bi-specific antigen-binding polypeptide of the invention.

In certain embodiments, the bi-specific antigen-binding polypeptides further comprise an antibody light chain. In certain embodiments, the light chain is naturally paired with the heavy chain through the natural light chain/heavy chain dimer interface, in the same way as this pairing occurs in a naturally-occurring, tetrameric antibody molecule. Exemplary bi-specific antigen-binding polypeptides having this structure are depicted in FIGS. 1 and 4, herein.

The first and second antigens can be the same or different. If the antigens are different, they can be in different regions of the same molecule or on different molecules. In certain embodiments, the first and second antigens are cell surface receptors. In certain embodiments, the first antigen is PDGFRβ or HER2 (e.g., human PDGFRβ or HER2). In certain embodiments, the second antigen is PDGFRβ or HER2 (e.g., human PDGFRβ or HER2). In one particular embodiment, the first antigen is PDGFRβ and the second antigen is HER2. In another particular embodiment, the first antigen is HER2 and the second antigen is PDGFRβ.

In certain embodiments, one antigen (the first or second antigen) is a cell surface receptor and one antigen (first or second) is a ligand (e.g., a growth factor, such as VEGF, PDGF, or EGF). In certain embodiments, the first antigen is PDGFRβ or VEGF (e.g., human PDGFRβ or VEGF). In certain embodiments, the second antigen is PDGFRβ or VEGF (e.g., human PDGFRβ or VEGF). In one particular embodiment, the first antigen is PDGFRβ and the second antigen is VEGF. In another particular embodiment, the first antigen is VEGF and the second antigen is PDGFRβ. Such bi-specific antigen-binding polypeptides are particularly useful for treating PDGFRβ-associated and VEGF-associated disorders, such as AMD and cancer.

The first and third antigens can be in different regions of the same molecule or on different molecules. In certain embodiments, the light chain binds to the first antigen and the heavy and light chains cooperate to create a single binding site for the second antigen. In certain embodiments, the light chain binds to a third antigen. It should be noted that if the first, second and third antigens are different, this allows for the production of antigen-binding polypeptides with three specificities. Such molecules are also encompassed by the invention.

Any antibody heavy chain, light chain, VH domain, VL domain, or CDR amino acid sequence can be used in the antigen-binding polypeptides of the invention. Exemplary antibody heavy chain, light chain, VH domain, VL domain, and CDR amino acid sequences are set forth in Tables 1-4, herein.

In certain embodiments, the bispecific antigen-binding polypeptide comprises an anti-PDGFRβ VH domain disclosed herein (e.g., as set forth in SEQ ID No: 24) and the VH and VL domains of an antibody that binds to an EGFR family receptor protein (e.g., EGFR, HER2, HER3, and/or HER4). Suitable therapeutic antibodies from which the VH and VL domains can be obtained include, without limitation, Trastuzumab (CAS#180288-69-1), Pertuzumab (CAS#380610-27-5), and Cetuximab (CAS#205923-56-4). In one particular embodiment, the bispecific antigen-binding polypeptide is formatted as set forth in FIG. 4.

Figure 12:
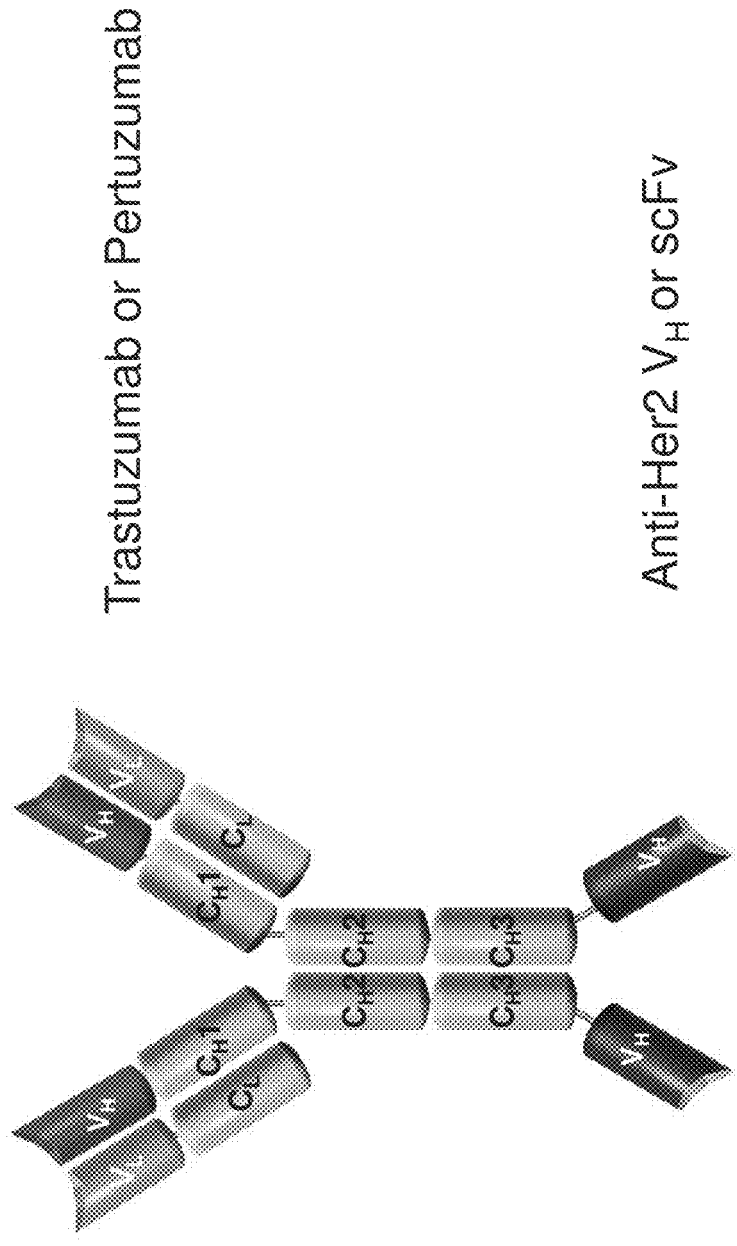
FIG. 12 is a schematic representation of an exemplary anti-HER2 bi-specific antigen-binding polypeptide of the invention.

In certain embodiments, the bispecific antigen-binding polypeptide comprises an anti-HER2 VH domain disclosed herein (e.g., those set forth in SEQ ID Nos: 13-16) and the VH and VL of an antibody that binds to an EGFR family member (e.g., EGFR, HER2, HER3, and/or HER4). Suitable therapeutic antibodies from which the VH and VL domains can be obtained include, without limitation, Trastuzumab (CAS#180288-69-1), Pertuzumab (CAS#380610-27-5), and Cetuximab (CAS#205923-56-4). In one particular embodiment, the bispecific antigen-binding polypeptide is formatted as set forth in FIG. 12.

TABLE 3

CDR, VH and VL amino acid sequences of exemplary anti-PDGFRβ VH and VL domains.

| Identifier | Amino acid sequence | SEQ ID NO. |
|---|---|---|
| XB2202 VH | QVQLVQSGAEVKKPGSSVRVSCKASGGTFSRHAISWVRQAPGQGLE WIGGILPILKTPNYAQRFQGRVTINADESTSTVYMEMSSLRSEDTA VYYCATHGGDRSYWGQGTLVTVSS | 24 |

TABLE 3-continued

CDR, VH and VL amino acid sequences of exemplary anti-PDGFRβ VH and VL domains.

| Identifier | Amino acid sequence | SEQ ID NO. |
|---|---|---|
| XB2202 HCDR3 | HGGDRSY | 25 |
| XB2202 HCDR2 | GILPILKTPNYAQRFQG | 26 |
| XB2202 HCDR1 | RHAIS | 27 |
| A4 VL | DVVMTQSPSSLSASVGDRVTITCQASQDISNWLNWYQQKPGKAPKL LIYEASNLETGVPSRFSGSGSGTDFTFTISSLQPEDIATYYCQQYN NVLRTFGQGTKVEIK | 28 |
| A4 LCDR3 | QQYNNVLRT | 29 |
| A4 LCDR3 | EASNLET | 30 |
| A4 LCDR3 | QASQDISNWLN | 31 |

TABLE 4

Heavy chain and light chain amino acid sequences of exemplary bi-specific antigen-binding polypeptides.

| Clone name | Amino Acid Sequence (Signal sequence underlined) | SEQ ID NO. |
|---|---|---|
| Format-1 and 2 Heavy chain | METDTLLLWVLLLWVPGSTGQVQLVQSGAEVKKPGSSVRVSCKASGGTFSRHAIS WVRQAPGQGLEWIGGILPILKTPNYAQRFQGRVTINADESTSTVYMEMSSLRSED TAVYYCATHGGDRSYWGQGTLVTVSSASTKGPSVFPLAPSSKSTSGGTAALGCLV KDYFPEPVTVSWNSGALTSGVHTFPAVLQSSGLYSLSSVVTVPSSSLGTQTYICN VNHKPSNTKVDKRVEPKSCDKTHTCPPCPAPELLGGPSVFLFPPKPKDTLMISRT PEVTCVVVDVSHEDPEVKFNWYVDGVEVHNAKTKPREEQYNSTYRVVSVLTVLHQ DWLNGKEYKCKVSNKALPAPIEKTISKAKGQPREPQVYTLPPSREEMTKNQVSLT CLVKGFYPSDIAVEWESNGQPENNYKTTPPVLDSDGSFFLYSKLTVDKSRWQQGN VFSCSVMHEALHNHYTQKSLSLSPGKGGGGSGGGGSGGGGSGGGGSEVQLVESGA EVKEPGASVKVSCKSSGYSFTGNYMHWVRQAPGQGLEWMGWMNPKSGGTYYAQKF QGRVTMTWDTSISTAYMELSGLTSDDTAVYYCARWARGSTSPHGLDVWGQGTLVT VSS | 17 |
| Format-1 and 2 Heavy chain minus signal sequence | QVQLVQSGAEVKKPGSSVRVSCKASGGTFSRHAISWVRQAPGQGLEWIGGILPIL KTPNYAQRFQGRVTINADESTSTVYMEMSSLRSEDTAVYYCATHGGDRSYWGQGT LVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKRVEPKSCD KTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAP IEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSL SLSPGKGGGGSGGGGSGGGGSGGGGSEVQLVESGAEVKEPGASVKVSCKSSGYSF TGNYMHWVRQAPGQGLEWMGWMNPKSGGTYYAQKFQGRVTMTWDTSISTAYMELS GLTSDDTAVYYCARWARGSTSPHGLDVWGQGTLVTVSS | 18 |
| Format-3 Heavy chain | METDTLLLWVLLLWVPGSTGEVQLVESGAEVKEPGASVKVSCKSSGYSFTGNYMH WVRQAPGQGLEWMGWMNPKSGGTYYAQKFQGRVTMTWDTSISTAYMELSGLTSDD TAVYYCARWARGSTSPHGLDVWGQGTLVTVSSASTKGPSVFPLAPSSKSTSGGTA ALGCLVKDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPPKPKDT LMISRTPEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSREEMTK NQVSLTCLVKGFYPSDIAVEWESNGQPENNYKTTPPVLDSDGSFFLYSKLTVDKS RWQQGNVFSCSVMHEALHNHYTQKSLSLSPGKGGGGSGGGGSGGGGSGGGGSQVQ LVQSGAEVKKPGSSVRVSCKASGGTFSRHAISWVRQAPGQGLEWIGGILPILKTP NYAQRFQGRVTINADESTSTVYMEMSSLRSEDTAVYYCATHGGDRSYWGQGTLVT VSS | 19 |
| Format-3 Heavy chain minus signal sequence | EVQLVESGAEVKEPGASVKVSCKSSGYSFTGNYMHWVRQAPGQGLEWMGWMNPKS GGTYYAQKFQGRVTMTWDTSISTAYMELSGLTSDDTAVYYCARWARGSTSPHGLD VWGQGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKRV EPKSCDKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGKEYKCKVSN KALPAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHNH YTQKSLSLSPGKGGGGSGGGGSGGGGSGGGGSQVQLVQSGAEVKKPGSSVRVSCK | 20 |

TABLE 4-continued

Heavy chain and light chain amino acid sequences of exemplary bi-specific antigen-binding polypeptides.

| Clone name | Amino Acid Sequence (Signal sequence underlined) | SEQ ID NO. |
|---|---|---|
| | ASGGTFSRHAISWVRQAPGQGLEWIGGILPILKTPNYAQRFQGRVTINADESTST VYMEMSSLRSEDTAVYYCATHGGDRSYWGQGTLVTVSS | |
| Format-1 Light chain | METDTLLLWVLLLWVPGSTGDVVMTQSPSSLSASVGDRVTITCQASQDISNWLNW YQQKPGKAPKLLIYEASNLETGVPSRFSGSGSGTDFTFTISSLQPEDIATYYCQQ YNNVLRTFGQGTKLEIKRTVAAPSVFIFPPSDEQLKSGTASVVCLLNNFYPREAK VQWKVDNALQSGNSQESVTEQDSKDSTYSLSSTLTLSKADYEKHKVYACEVTHQG LSSPVTKSFNRGEC | 21 |
| Format-1 Light chain minus signal sequence | DVVMTQSPSSLSASVGDRVTITCQASQDISNWLNWYQQKPGKAPKLLIYEASNLE TGVPSRFSGSGSGTDFTFTISSLQPEDIATYYCQQYNNVLRTFGQGTKLEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC | 22 |
| Heavy chain Linker | GGGGSGGGGSGGGGSGGGGS | 23 |

In certain embodiments, the bi-specific antigen-binding polypeptides of the invention comprise a first VH domain and/or second VH domain that binds specifically to human HER2. In certain embodiments, the anti-HER2 VH domain comprises the HCDR3 amino acid sequence set forth in SEQ ID NO:1, 4, 7, or 10, together with a HCDR2 and/or a HCDR1 sequence independently selected from any one of the heavy chain HCDR2 or HCDR1 amino acid sequences set forth in Table 1. In certain embodiments, the anti-HER2 VH domain comprises HCDR3, HCDR2 and HCDR1 amino acid sequences selected from the group consisting of SEQ ID NO: 1, 2 and 3; 4, 5 and 6; 7, 8 and 9; and 10, 11 and 12, respectively. In certain embodiments, the anti-HER2 VH domain comprises the amino acid sequence set forth in SEQ ID NO: 13, 14, 15, or 16.

In certain embodiments, the bi-specific antigen-binding polypeptides of the invention comprise a first VH domain and/or second VH domain that binds specifically to human PDGFRβ. Any VH domain that binds to PDGFRβ can be used in the methods of the invention. Suitable VH domains include those set forth in U.S. application Ser. No. 13/705,978 filed on Dec. 5, 2012, which is herein incorporated by reference in its entirety. In certain embodiments, the anti-PDGFRβ VH domain comprises the HCDR3 amino acid sequence set forth in SEQ ID NO: 25. In certain embodiments, the anti-PDGFRβ VH domain comprises the HCDR3, HCDR2 and HCDR1 amino acid sequences set forth in SEQ ID NO: 25, 26, and 27, respectively. In certain embodiments, the anti-PDGFRβ VH domain comprises the amino acid sequence set forth in SEQ ID NO: 24.

In certain embodiments, the bi-specific antigen-binding polypeptides of the invention comprise a VL that binds specifically to human PDGFRβ. Any VL domain that binds to PDGFRβ can be used in the methods of the invention. Suitable VL domains include those set forth in U.S. application Ser. No. 13/705,978 filed on Dec. 5, 2012. In certain embodiments, the anti-PDGFRβ VH domain comprises the HCDR3 amino acid sequence set forth in SEQ ID NO: 25. In certain embodiments, the anti-PDGFRβ VL domain comprises the HCDR3, HCDR2 and HCDR1 amino acid sequences set forth in SEQ ID NO: 29, 30, and 31, respectively. In certain embodiments, the anti-PDGFRβ VL domain comprises the amino acid sequence set forth in SEQ ID NO: 28.

In one particular embodiment, the bi-specific antigen-binding polypeptides of the invention comprise the heavy chain set forth in SEQ ID NO: 18 or 20.

In one particular embodiment, the bi-specific antigen-binding polypeptides of the invention comprise the antibody light chain set forth in SEQ ID NO: 22.

In certain embodiments, the bi-specific antigen-binding polypeptides of the invention comprise one or more CDR, VH domain, VL domain, heavy chain or light chain comprising at least one or more conservative amino acid substitutions (e.g., 1, 2, 3, 4, 5, etc, conservative amino acid substitutions). Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in an anti-PDGFRβ antibody is preferably replaced with another amino acid residue from the same class. Methods of identifying amino acid conservative substitutions which do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:412-417 (1997), each of which is incorporated by reference herein in its entirety).

In certain embodiments, the present invention provides bi-specific antigen-binding polypeptides that comprise CDR, VH domain, VL domain, heavy chain, or light chain amino acid sequences with about 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the CDR, VH domain, VL domain, heavy chain or light chain amino acid sequences disclosed herein.

IV. Modified Antigen-Binding Polypeptides

In certain embodiments, antigen-binding polypeptides of the invention may comprise one or more modifications. Modified forms of antigen-binding polypeptides of the invention can be made using any techniques known in the art.

i) Reducing Immunogenicity

In certain embodiments, antigen-binding polypeptides (e.g., bi-specific antigen-binding polypeptides, antibodies or antigen binding fragments thereof) of the invention are modified to reduce their immunogenicity using art-recognized techniques. For example, antibodies, or fragments thereof, can be chimericized, humanized, and/or deimmunized.

In one embodiment, an antibody, or antigen binding fragments thereof, of the invention may be chimeric. A chimeric antibody is an antibody in which different portions of the antibody are derived from different animal species, such as antibodies having a variable region derived from a murine monoclonal antibody and a human immunoglobulin constant region. Methods for producing chimeric antibodies, or fragments thereof, are known in the art. See, e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397, which are incorporated herein by reference in their entireties. Techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) may be employed for the synthesis of said molecules. For example, a genetic sequence encoding a binding specificity of a mouse anti-PDGFRβ antibody molecule may be fused together with a sequence from a human antibody molecule of appropriate biological activity. As used herein, a chimeric antibody is a molecule in which different portions are derived from different animal species, such as those having a variable region derived from a murine monoclonal antibody and a human immunoglobulin constant region, e.g., humanized antibodies.

In another embodiment, an antibody, or antigen binding portion thereof, of the invention is humanized. Humanized antibodies have a binding specificity comprising one or more complementarity determining regions (CDRs) from a non-human antibody and framework regions from a human antibody molecule. Often, framework residues in the human framework regions will be substituted with the corresponding residue from the CDR donor antibody to alter, and preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties). Antibodies can be humanized using a variety of techniques known in the art including, for example, CDR-grafting (EP 239,400; PCT publication WO 91/09967; U.S. Pat. Nos. 5,225,539; 5,530,101; and 5,585,089, which are incorporated herein by reference in their entireties), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994), which are incorporated herein by reference in their entireties), and chain shuffling (U.S. Pat. No. 5,565,332, which is incorporated herein by reference in its entirety).

In some embodiments, de-immunization can be used to decrease the immunogenicity of PDGFRβ antigen-binding polypeptides (e.g., antibody, or antigen binding portion thereof). As used herein, the term "de-immunization" includes alteration of polypeptide (e.g., an antibody, or antigen binding portion thereof) to modify T cell epitopes (see, e.g., WO9852976A1, WO0034317A2, which are incorporated herein by reference in their entireties). For example, VH and VL sequences from the starting PDGFRβ-specific antibody, or antigen binding portion thereof, of the invention may be analyzed and a human T cell epitope "map" may be generated from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of antigen-binding polypeptides for use in the diagnostic and treatment methods disclosed herein, which are then tested for function. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

ii) Effector Functions and Fc Modifications

Antigen-binding polypeptides of the invention generally comprise an antibody constant region (e.g. an IgG constant region e.g., a human IgG constant region, e.g., a human IgG1, 2, 3 or 4 constant region) which mediates one or more effector functions. For example, binding of the C1 component of complement to an antibody constant region may activate the complement system. Activation of complement is important in the opsonisation and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. In preferred embodiments, the antigen-binding polypeptides (e.g., antibodies or antigen binding fragments thereof) of the invention bind to an Fc-gamma receptor. In alternative embodiments, antigen-binding polypeptides of the invention may comprise a constant region that is devoid of one or more effector functions (e.g., ADCC activity) and/or is unable to bind Fcγ receptor.

Certain embodiments of the invention include antigen-binding polypeptides in which at least one amino acid in one or more of the constant region domains has been deleted or otherwise altered so as to provide desired biochemical characteristics such as reduced or enhanced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies, or fragments thereof, for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain other embodiments, antigen-binding polypeptides comprise constant regions derived from different antibody isotypes (e.g., constant regions from two or more of a human IgG1, IgG2, IgG3, or IgG4). In other embodiments, antigen-binding polypeptides comprise a chimeric hinge (i.e., a hinge comprising hinge portions derived from hinge domains of different antibody isotypes, e.g., an upper hinge domain from an IgG4 molecule and an IgG1 middle hinge domain). In one embodiment, antigen-binding polypeptides comprise an Fc region or portion thereof from a human IgG4 molecule and a Ser228Pro mutation (EU numbering) in the core hinge region of the molecule.

In certain embodiments, the Fc portion may be mutated to increase or decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or flexibility. The resulting physiological profile, bioavailability and other biochemical effects of the modifications, such as tumor localization, biodistribution and serum half-life, may easily be measured and quantified using well known immunological techniques without undue experimentation.

In certain embodiments, an Fc domain employed in an antibody of the invention is an Fc variant. As used herein, the term "Fc variant" refers to an Fc domain having at least one amino acid substitution relative to the wild-type Fc domain from which said Fc domain is derived. For example, wherein the Fc domain is derived from a human IgG1 antibody, the Fc variant of said human IgG1 Fc domain comprises at least one amino acid substitution relative to said Fc domain.

The amino acid substitution(s) of an Fc variant may be located at any position (i.e., any EU convention amino acid position) within the Fc domain. In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

The antigen-binding polypeptides of the invention may employ any art-recognized Fc variant which is known to impart an improvement (e.g., reduction or enhancement) in effector function and/or FcR binding. The Fc variants may include, for example, any one of the amino acid substitutions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO05/070963A1, WO05/077981A2, WO05/092925A2, WO05/123780A2, WO06/019447A1, WO06/047350A2, and WO06/085967A2 or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784, each of which is incorporated by reference herein in its entirety. In one exemplary embodiment, a binding polypeptide of the invention may comprise an Fc variant comprising an amino acid substitution at EU position 268 (e.g., H268D or H268E). In another exemplary embodiment, a binding polypeptide of the invention may comprise an amino acid substitution at EU position 239 (e.g., S239D or S239E) and/or EU position 332 (e.g., I332D or I332Q).

In certain embodiments, an antigen-binding polypeptide of the invention may comprise an Fc variant comprising an amino acid substitution which alters the antigen-independent effector functions of the antibody, in particular the circulating half-life of the binding polypeptide. Such antigen-binding polypeptides exhibit either increased or decreased binding to FcRn when compared to antigen-binding polypeptides lacking these substitutions, therefore, have an increased or decreased half-life in serum, respectively. Fc variants with improved affinity for FcRn are anticipated to have longer serum half-lives, and such molecules have useful applications in methods of treating mammals where long half-life of the administered antigen-binding polypeptide is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the altered antigen-binding polypeptides of the invention exhibit reduced transport across the epithelium of kidney glomeruli from the vasculature. In another embodiment, the altered antigen-binding polypeptides of the invention exhibit reduced transport across the blood brain barrier (BBB) from the brain, into the vascular space. In one embodiment, an antibody with altered FcRn binding comprises an Fc domain having one or more amino acid substitutions within the "FcRn binding loop" of an Fc domain. The FcRn binding loop is comprised of amino acid residues 280-299 (according to EU numbering). Exemplary amino acid substitutions which altered FcRn binding activity are disclosed in International PCT Publication No. WO05/047327 which is incorporated by reference herein. In certain exemplary embodiments, the antigen-binding polypeptides of the invention comprise an Fc domain having one or more of the following substitutions: V284E, H285E, N286D, K290E and S304D (EU numbering).

In other embodiments, antigen-binding polypeptides for use in the diagnostic and treatment methods described herein have a constant region, e.g., an IgG1 heavy chain constant region, which is altered to reduce or eliminate glycosylation. For example, antigen-binding polypeptides of the invention may also comprise an Fc variant comprising an amino acid substitution that alters the glycosylation of the antibody Fc. For example, said Fc variant may have reduced glycosylation (e.g., N- or O-linked glycosylation). In exemplary embodiments, the Fc variant comprises reduced glycosylation of the N-linked glycan normally found at amino acid position 297 (EU numbering). In another embodiment, the antigen-binding polypeptide has an amino acid substitution near or within a glycosylation motif, for example, an N-linked glycosylation motif that contains the amino acid sequence NXT or NXS. In a particular embodiment, the antigen-binding polypeptide comprises an Fc variant with an amino acid substitution at amino acid position 228 or 299 (EU numbering). In more particular embodiments, the antigen-binding polypeptide comprises an IgG1 or IgG4 constant region comprising an S228P and a T299A mutation (EU numbering).

Exemplary amino acid substitutions which confer reduced or altered glycosylation are disclosed in International PCT Publication No. WO05/018572, which is incorporated by reference herein in its entirety. In preferred embodiments, the antigen-binding polypeptides of the invention are modified to eliminate glycosylation. Such antigen-binding polypeptides may be referred to as "agly" antigen-binding polypeptides. While not being bound by theory, it is believed that "agly" antigen-binding polypeptides may have an improved safety and stability profile in vivo. Exemplary agly antigen-binding polypeptides comprise an aglycosylated Fc region of an IgG4 antibody which is devoid of Fc-effector function thereby eliminating the potential for Fc mediated toxicity to the normal vital organs that express PDGFRβ. In yet other embodiments, antigen-binding polypeptides of the invention comprise an altered glycan. For example, the antigen-binding polypeptide may have a reduced number of fucose residues on an N-glycan at Asn297 of the Fc region, i.e., is afucosylated. In another embodiment, the antigen-binding polypeptide may have an altered number of sialic acid residues on the N-glycan at Asn297 of the Fc region.

iii) Covalent Attachment

Antigen-binding polypeptides of the invention may be modified, e.g., by the covalent attachment of a molecule to the binding polypeptide such that covalent attachment does not prevent the binding polypeptide from specifically binding to its cognate epitope. For example, but not by way of limitation, the antigen-binding polypeptide of the invention may be modified by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

Antigen-binding polypeptides of the invention may further be recombinantly fused to a heterologous polypeptide at the N- or C-terminus or chemically conjugated (including covalent and non-covalent conjugations) to polypeptides or other compositions. For example, antigen-binding polypeptides may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387, each of which is incorporated herein by reference in its entirety.

Antigen-binding polypeptides may be fused to heterologous polypeptides to increase the in vivo half-life or for use in immunoassays using methods known in the art. For example, in one embodiment PEG can be conjugated to the antigen-binding polypeptides of the invention to increase their half-life in vivo (see Leong, S. R., et al., Cytokine 16:106 (2001); Adv. in Drug Deliv. Rev. 54:531 (2002); or Weir et al., Biochem. Soc. Transactions 30:512 (2002), which are incorporated by reference herein in their entireties.

Moreover, antigen-binding polypeptides of the invention can be fused to marker sequences, e.g., a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989) (which is incorporated by reference herein in its entirety), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984), which is incorporated by reference herein in its entirety) and the "flag" tag.

Antigen-binding polypeptides of the invention may be used in non-conjugated form or may be conjugated to at least one of a variety of molecules, e.g., to improve the therapeutic properties of the molecule, to facilitate target detection, or for imaging or therapy of the patient. Antigen-binding polypeptides of the invention can be labeled or conjugated either before or after purification, when purification is performed. In particular, antigen-binding polypeptides of the invention may be conjugated to therapeutic agents, prodrugs, peptides, proteins, enzymes, viruses, lipids, biological response modifiers, pharmaceutical agents, or PEG.

The present invention further encompasses antigen-binding polypeptides of the invention conjugated to a diagnostic or therapeutic agent. The antigen-binding polypeptides can be used diagnostically to, for example, monitor the development or progression of a immune cell disorder (e.g., CLL) as part of a clinical testing procedure to, e.g., determine the efficacy of a given treatment and/or prevention regimen. Detection can be facilitated by coupling the antigen-binding polypeptides to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 (which is incorporated by reference herein in its entirety) for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Antigen-binding polypeptides for use in the diagnostic and treatment methods disclosed herein may be conjugated to cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), or PEG.

In another embodiment, antigen-binding polypeptides for use in the diagnostic and treatment methods disclosed herein can be conjugated to a molecule that decreases tumor cell growth. In other embodiments, the disclosed compositions may comprise antibodies, or fragments thereof, coupled to drugs or prodrugs. Still other embodiments of the present invention comprise the use of antigen-binding polypeptides conjugated to specific biotoxins or their cytotoxic fragments such as ricin, gelonin, *Pseudomonas* exotoxin or diphtheria toxin. The selection of which conjugated or unconjugated antibody to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that, in previous studies, anti-tumor antibodies labeled with isotopes have been used successfully to destroy tumor cells in animal models, and in some cases in humans. Exemplary radioisotopes include: $^{90}$Y, $^{125}$I, $^{131}$I, $^{123}$I, $^{111}$In, $^{105}$Rh $^{153}$Sm, $^{67}$Cu, $^{67}$Ga, $^{166}$Ho, $^{177}$Lu, $^{186}$Re and $^{188}$Re. The radionuclides act by producing ionizing radiation which causes multiple strand breaks in nuclear DNA, leading to cell death. The isotopes used to produce therapeutic conjugates typically produce high energy alphaor beta-particles which have a short path length. Such radionuclides kill cells to which they are in close proximity, for example neoplastic cells to which the conjugate has attached or has entered. They have little or no effect on non-localized cells. Radionuclides are essentially non-immunogenic.

V. Expression of Antigen-Binding Polypeptides

Following manipulation of the isolated genetic material to provide antigen-binding polypeptides of the invention as set forth above, the genes are typically inserted in an expression vector for introduction into host cells that may be used to produce the desired quantity of the antigen-binding polypeptides.

The term "vector" or "expression vector" is used herein for the purposes of the specification and claims to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems may be employed for the purposes of this invention. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, transcriptional promoters, enhancers, and termination signals. In particularly preferred embodiments the cloned variable region genes are inserted into an expression vector along with the heavy and light chain constant region genes (preferably human) synthesized as discussed above.

In other preferred embodiments the antigen-binding polypeptide of the invention may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is incorporated herein by reference in its entirety. Those skilled in the art will appreciate that such expression systems may be used to effectively produce the full range of polypeptides disclosed in the instant application.

More generally, once a vector or DNA sequence encoding an antibody, or fragment thereof, has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Chapter 24.2, pp. 470-472 Vectors, Rodriguez and Denhardt, Eds. (Butterworths, Boston, Mass. 1988), which is incorporated by reference herein in its entirety. Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

In one embodiment, the host cell line used for antigen-binding polypeptide expression is of mammalian origin; those skilled in the art can determine particular host cell lines which are best suited for the desired gene product to be expressed therein. Exemplary host cell lines include, but are not limited to, DG44 and DUXB 11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), BFA-1c1BPT (bovine endothelial cells), RAJI (human lymphocyte), 293 (human kidney). In one embodiment, the cell line provides for altered glycosylation, e.g., afucosylation, of the antibody expressed therefrom (e.g., PER.C6® (Crucell) or FUT8-knock-out CHO cell lines (Potelligent® Cells) (Biowa, Princeton, N.J.)). In one embodiment NSO cells may be used. CHO cells are particularly preferred. Host cell lines are typically available from commercial services, the American Tissue Culture Collection or from published literature.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-) affinity chromatography.

Genes encoding the antigen-binding polypeptides of the invention can also be expressed in non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the polypeptides can become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980), each of which are incorporated by reference herein in its entirety) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977), which is incorporated by reference herein in its entirety). The presence of the trpl lesion as a characteristic of the yeast host cell genome then provides an effective environment for detecting transformation by growth in the absence of tryptophan.

VI. Pharmaceutical Formulations and Methods of Administration of Antigen-Binding Polypeptides In another aspect, the invention provides pharmaceutical compositions comprising the antigen-binding polypeptides disclosed herein.

Methods of preparing and administering antigen-binding polypeptides of the invention to a subject are well known to or are readily determined by those skilled in the art. The route of administration of the antigen-binding polypeptides of the invention may be oral, parenteral, inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the antigen-binding polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an antibody by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. Nos. 09/259,337 and 09/259,338 each of which is incorporated herein by reference in its entirety. Such articles of manufacture will preferably have labels or package inserts indicating that the associated compositions are useful for treating a subject suffering from, or predisposed to autoimmune or neoplastic disorders.

Effective doses of the stabilized antigen-binding polypeptides of the present invention for the treatment of the above described conditions vary depending upon many different factors including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

For passive immunization with an antibody of the invention, the dosage may range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of subject body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention.

Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more antigen-binding polypeptides with different binding specificities are administered simultaneously, in which case the dosage of each antibody administered may fall within the ranges indicated.

Antigen-binding polypeptides of the invention can be administered on multiple occasions. Intervals between single dosages can be, e.g., daily, weekly, monthly or yearly. Intervals can also be irregular as indicated by measuring blood levels of polypeptide or target molecule in the patient.

In some methods, dosage is adjusted to achieve a certain plasma antibody or toxin concentration, e.g., 1-1000 ug/ml or 25-300 ug/ml. Alternatively, antigen-binding polypeptides can be administered as a sustained release formulation, in which case less frequent administration is required. Dosage and frequency vary depending on the half-life of the antigen-binding polypeptide in the patient. In general, humanized antigen-binding polypeptides show the longest half-life, followed by chimeric antigen-binding polypeptides and nonhuman antigen-binding polypeptide. In one embodiment, the antigen-binding polypeptides of the invention can be administered in unconjugated form. In another embodiment, the antigen-binding polypeptides of the invention can be administered multiple times in conjugated form. In still another embodiment, the antigen-binding polypeptides of the invention can be administered in unconjugated form, then in conjugated form, or vise versa.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding a polypeptide of the invention (e.g., in a vector). Doses for nucleic acids encoding polypeptides range from about 10 ng to 1 g, 100 ng to 100 mg, 1 ug to 10 mg, or 30-300 ug DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. Intramuscular injection or intravenous infusion are preferred for administration of a antibody of the invention. In some methods, therapeutic antibodies, or fragments thereof, are injected directly into the cranium. In some methods, antibodies, or fragments thereof, are administered as a sustained release composition or device, such as a Medipad™ device.

Antigen-binding polypeptides of the invention can optionally be administered in combination with other agents that are effective in treating the disorder or condition in need of treatment (e.g., prophylactic or therapeutic). Preferred additional agents are those which are art recognized and are standardly administered for a particular disorder.

Effective single treatment dosages (i.e., therapeutically effective amounts) of $^{90}$Y-labeled antibodies of the invention range from between about 5 and about 75 mCi, more preferably between about 10 and about 40 mCi. Effective single treatment non-marrow ablative dosages of $^{131}$I-labeled antigen-binding polypeptides range from between about 5 and about 70 mCi, more preferably between about 5 and about 40 mCi. Effective single treatment ablative dosages (i.e., may require autologous bone marrow transplantation) of $^{131}$I-labeled antibodies range from between about 30 and about 600 mCi, more preferably between about 50 and less than about 500 mCi.

While a great deal of clinical experience has been gained with $^{131}$I and $^{90}$Y, other radiolabels are known in the art and have been used for similar purposes. Still other radioisotopes are used for imaging. For example, additional radioisotopes which are compatible with the scope of the instant invention include, but are not limited to, $^{123}$I, $^{125}$I, $^{32}$P, $^{57}$Co, $^{64}$Cu, $^{67}$Cu, $^{77}$Br, $^{81}$Rb, $^{81}$K, $^{87}$Sr, $^{113}$In, $^{127}$Cs, $^{129}$Cs, $^{132}$I, $^{197}$Hg, $^{206}$Bi, $^{177}$Lu, $^{186}$Re, $^{212}$Pb, $^{212}$Bi, $^{47}$Sc, $^{105}$Rh $^{109}$Pd, $^{153}$Sm, $^{188}$Re, $^{199}$Au, $^{225}$Ac, $^{211}$A, and $^{213}$Bi. In this respect alpha, gamma and beta emitters are all compatible with in the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include $^{125}$I, $^{123}$I, $^{99}$TC, $^{43}$K, $^{52}$Fe, $^{67}$Ga, $^{68}$Ga, as well as $^{111}$In. Antibodies have also been labeled with a variety of radionuclides for potential use in targeted immunotherapy (Peirersz et al. Immunol. Cell Biol. 65: 111-125 (1987), which is incorporated herein by reference in its entirety). These radionuclides include $^{188}$Re and $^{186}$Re as well as $^{199}$Au and $^{67}$Cu to a lesser extent. U.S. Pat. No. 5,460,785 provides additional data regarding such radioisotopes and is incorporated herein by reference in its entirety.

As previously discussed, the antigen-binding polypeptides of the invention can be administered in a pharmaceutically effective amount for the in vivo treatment of mammalian disorders. In this regard, it will be appreciated that the disclosed antigen-binding polypeptides will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of an antigen-binding polypeptide of the invention, conjugated or unconjugated to a therapeutic agent, shall be held to mean an amount sufficient to achieve effective binding to a target and to achieve a benefit, e.g., to ameliorate symptoms of a disease or disorder or to detect a substance or a cell. In the case of tumor cells, the polypeptide will be preferably be capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the polypeptide.

In keeping with the scope of the present disclosure, the antigen-binding polypeptides of the invention may be administered to a human or other animal in accordance with the aforementioned methods of treatment in an amount sufficient to produce a therapeutic or prophylactic effect. The antigen-binding polypeptides of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of polypeptides according to the present invention may prove to be particularly effective.

VII. Methods of Treating Diseases or Disorders

The antigen-binding polypeptides of the invention are useful for antagonizing the activity of cell surface receptors such as HER2 and/or PDGFRβ. Accordingly, in another aspect, the invention provides methods for treating PDGFRβ- and/or HER2-associated diseases or disorders by administering to a subject in need of thereof a pharmaceutical composition comprising one or more antigen-binding polypeptide of the invention.

In certain embodiments, the anti-PDGFRβ, anti-HER2, and/or bispecific antigen-binding polypeptides disclosed herein (e.g., those set forth in SEQ ID Nos: 13-16, 17-22, and/or 24) are administered in combination with additional therapeutic agents. Suitable therapeutic molecules include, without limitation, inhibitors of EGFR family receptor activity (e.g., Trastuzumab (CAS#180288-69-1), Pertuzumab (CAS#380610-27-5), Cetuximab (CAS#205923-56-4), and Erlotinib (CAS#183321-74-6). In one particular embodiment, an anti-PDGFRβ/anti-HER2 bispecific antigen-binding polypeptide is administered in combination with Trastuzumab and/or Pertuzumab. In one particular embodiment, an anti-HER2 monospecific antigen-binding polypeptide is administered in combination with Trastuzumab and/or Pertuzumab.

Diseases or disorders amenable to treatment include, without limitation cancer, e.g., breast and ovarian cancer.

One skilled in the art would be able, by routine experimentation, to determine what an effective, non-toxic amount of antibody (or additional therapeutic agent) would be for the purpose of treating a PDGFRβ- and/or HER2-associated disease or disorder. For example, a therapeutically active amount of a polypeptide may vary according to factors such as the disease stage (e.g., stage I versus stage IV), age, sex, medical complications (e.g., immunosuppressed conditions or diseases) and weight of the subject, and the ability of the antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10, milligrams per kilogram body weight per day.

VIII. EXAMPLES

The present invention is further illustrated by the following examples which should not be construed as further limiting. The contents of Sequence Listing, figures and all references, patents and published patent applications cited throughout this application are expressly incorporated herein by reference.

Example 1

Production of HER2/PDGFRβ Bi-Specific Antigen-Binding Polypeptides

Figure 5:
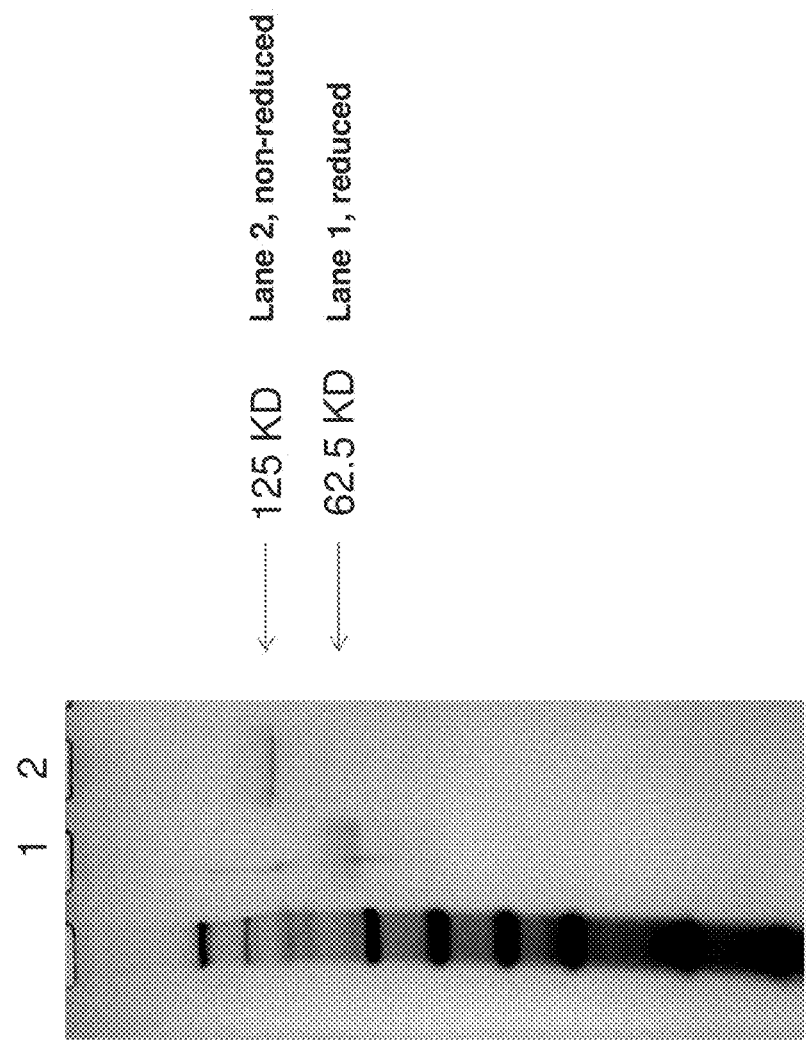
FIG. 5 depicts an SDS-PAGE gel of an exemplary bi-specific antigen-binding polypeptide of the invention under reducing and non-reducing conditions.

The genes coding for various HER2/PDGFRβ bi-specific antigen-binding polypeptide formats were synthesized and cloned into mammalian expression vectors. The constructs were then transiently transfected into HEK293 cells following the standard protocol. The supernatant was harvested and tested for expression. An SDS-PAGE gel of an expressed dimer of bi-specific format 2 (SEQ ID No 18 in Table 4) is set forth in FIG. 5. The gel shows that under non-reducing conditions a polypeptide of the expected 125 Da is expressed (lane 2) and that this dissociates into monomers of the expected 62.5 kDa under reducing conditions (lane 1).

Example 2

Figure 6:
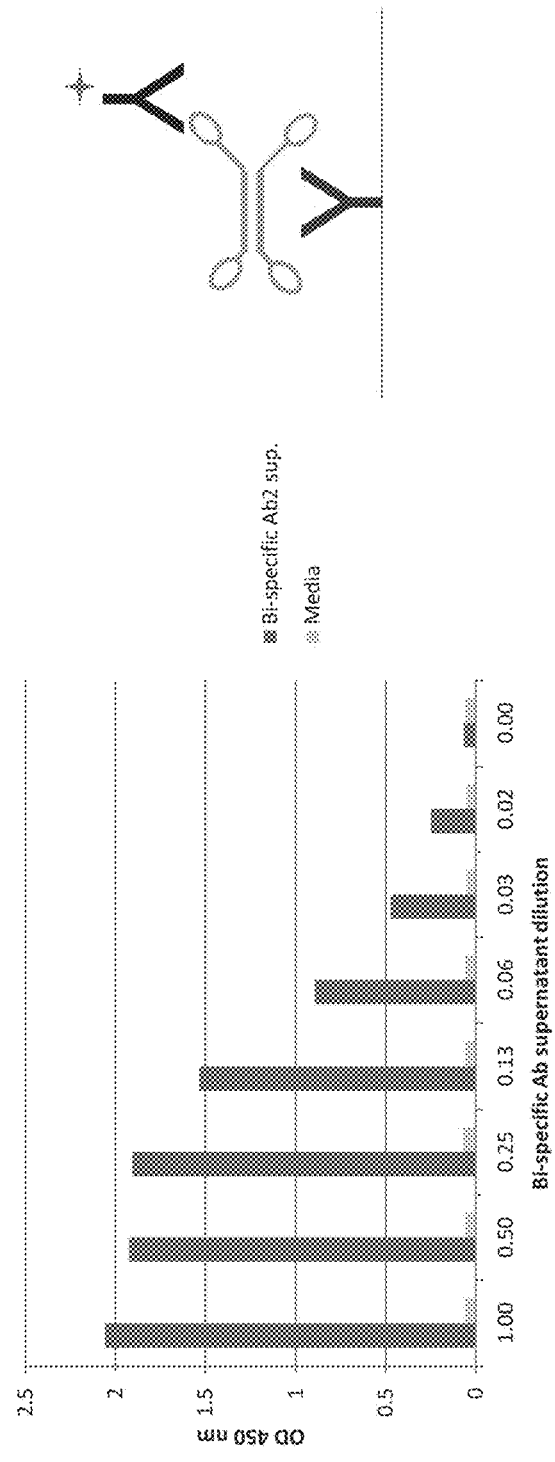
FIG. 6 shows the results of an ELISA assay detecting the expression of a HER2/PDGFRβ bi-specific antigen-binding polypeptide in HEK293 cell culture supernatant.

Assessment of HER2/PDGFRβ Bi-Specific Antigen-Binding Polypeptide Expression Using ELISA An ELISA assay was developed to assay the expression of the HER2/PDGFRβ bi-specific antigen-binding polypeptides in cell supernatant. Briefly, 2 ug/mL of anti-human Fc antibody was captured on a Maxisorp Immulon plate overnight and blocked with superblock. The supernatant was serially diluted and loaded onto the plate. Culture media was similarly diluted and loaded in parallel as a negative control. The bi-specific antigen-binding polypeptide was detected with anti-human Fab specific HRP. The results set forth in FIG. 6 show that the ELISA assay is able to detect bi-specific antigen-binding polypeptide in HEK293 cell supernatant.

Example 3

Figure 7:
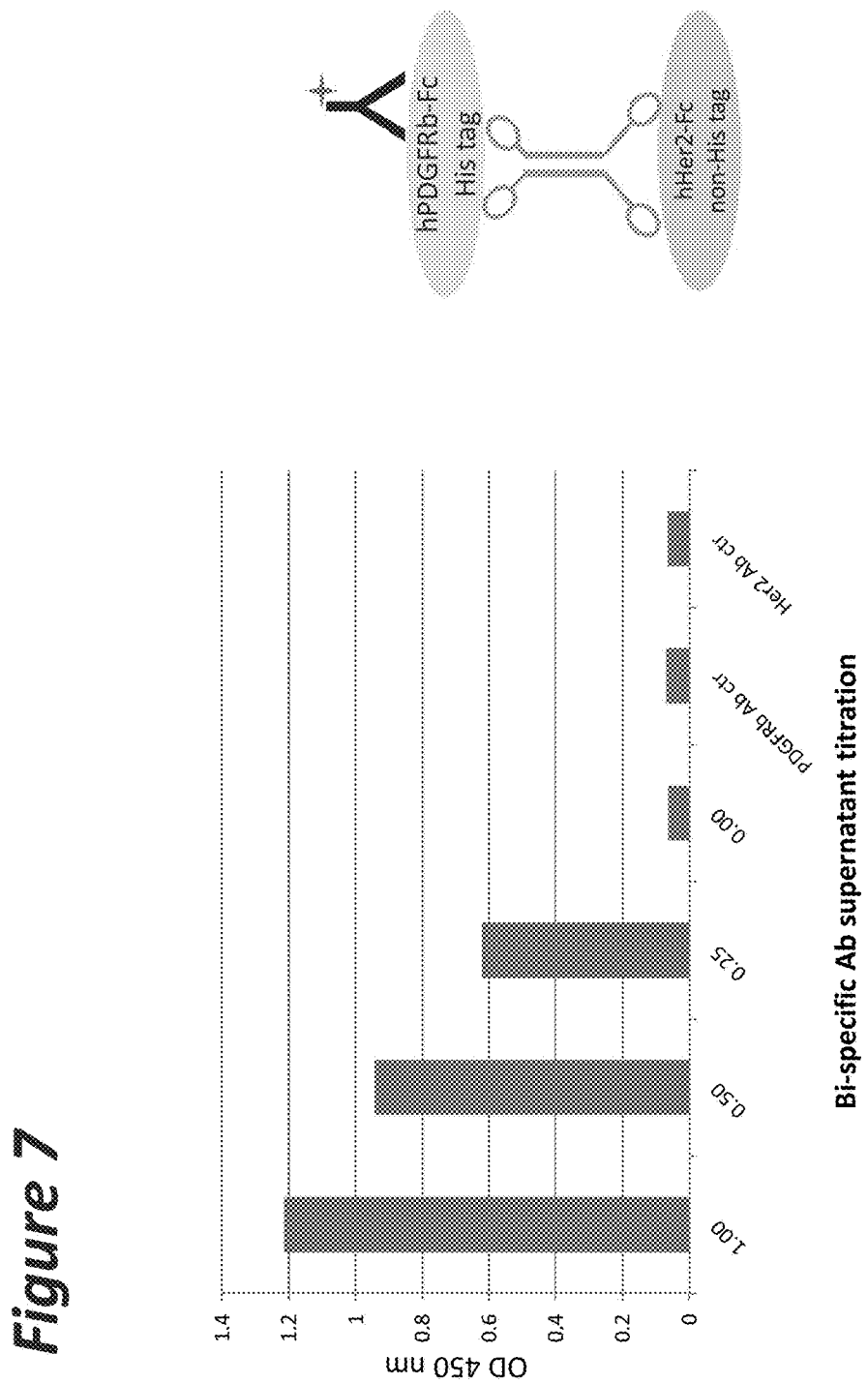
FIG. 7 shows the results of an ELISA assay measuring the simultaneous binding of HER2/PDGFRβ bi-specific antigen-binding polypeptide to HER2 and PDGFRβ.

Detection of Simultaneous Antigen Binding of HER2/PDGFRβ Bi-Specific Antigen-Binding Polypeptides Using ELISA An ELISA assay was developed to detect the simultaneous binding of HER2/PDGFRβ bi-specific antigen-binding polypeptides to HER2 and PDGFRβ. Briefly, 2 ug/mL of human Her2-Fc fusion protein (with no His epitope tag) was immobilized on a Maxisorp Immulon plate overnight and blocked with superblock. HEK293 cell supernatant containing a bi-specific antigen-binding polypeptide was serial diluted and loaded on the plate. After a one hour incubation, the plate was washed and 100 nM of human PDGFRβ-Fc fusion (with a His epitope tag) was applied to the plate and incubated for one hour. The binding of the bi-specific Ab to Her2 and PDGFRb was detected using an anti-His HRP. The results set forth in FIG. 7 show that the bi-specific antigen-binding polypeptide can simultaneously bind to both HER2 and PDGFRβ.

Example 4

FACS-based Binding Assay of HER2/PDGFRβ Bi-Specific Antigen-Binding Polypeptides An FACS-based binding assay was developed to detect the simultaneous binding of HER2/PDGFRβ bi-specific antigen-binding polypeptides to HER2 and PDGFRβ when expressed on the surface of cells. Specifically, 200 ul of HEK 293 cells constitutively over-expressing HER2 or HEK293 cells transiently over-expressing PFGFRβ, or mock transfected control cells were plated at one million cells per ml a fresh 96 well plate. Cells were maintained at 4° C. to avoid receptor internalization. HEK293 cell supernatants containing Format-2 or Format-3 HER2/PDGFRβ bi-specific antigen-binding polypeptides (see Table 4 and FIGS. 2 and 3) were incubated with 25 nM of recombinant human PDGFRβ-CF647 or recombinant human Her2-CF647 to allow bi-specific/labeled protein complexes to form. After incubation, 100 ul of each supernatant were added to the appropriate HER2-expressing, PDGFRβ-expressing, or control cells and incubated with shaking at 4° C. for two hours, to allow binding of the bi-specific/labeled protein complexes to cell surface HER2 and PDGFRβ. After incubation, cells were pelleted by centrifugation at 1500 rpm for 4 min, washed once with 200 ul of fresh full media, and resuspended in a final volume of 200 ul in fresh full media. The binding of the fluorescently labeled PDGFRβ-CF647 or Her2-CF647 to the cells was determined using a Guava flow cytometer (Millipore). A positive shift along the X-axis was considered to be indicative of association of labeled PDGFRβ-CF647 or Her2-CF647 with cells.

In these experiments, anti-PDGFR antibody or anti-HER2 antibody, media only and CF647-labeled receptor were used as negative controls. 25 nM CF647-labelled HER2 antibody or 50 nM CF647-labelled PDGFRβ antibody were used as positive controls on HER2 and PDGFRβ expressing cells, respectively.

Figure 8:
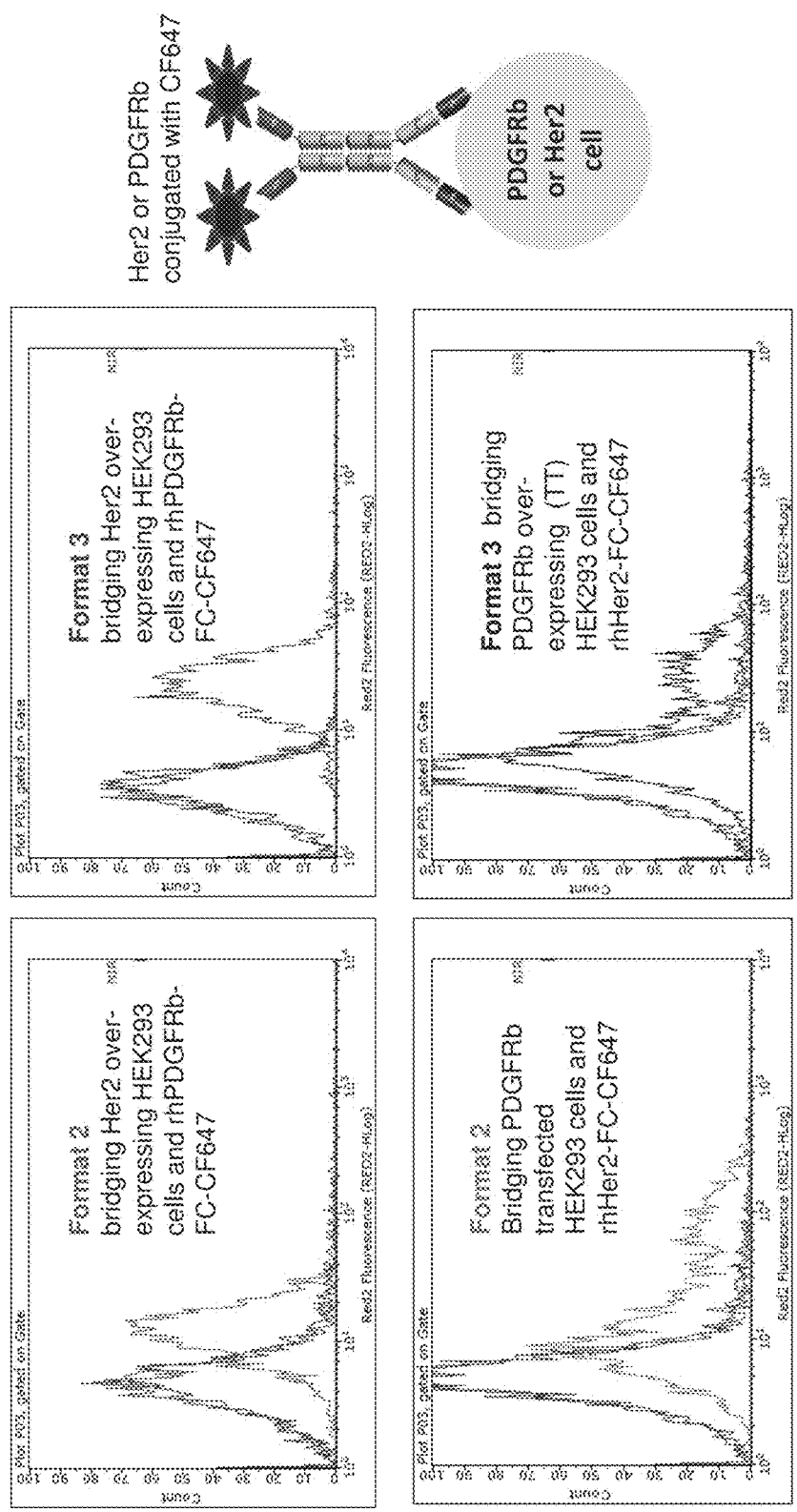
FIG. 8 shows the results of a FACS-based binding assay measuring the simultaneous binding of HER2/PDGFRβ bi-specific antigen-binding polypeptide to cell surface expressed HER2 and PDGFRβ.

The results of these experiments are set forth in FIG. 8. This data shows that both the Format-2 and Format-3 HER2/PDGFRβ bi-specific antigen-binding polypeptides were able to bind simultaneous to cell surface HER2 and PDGFRβ.

Example 4

Analysis of Binding of an Exemplary Anti-HER2 VH Domain to HER2

Figure 9:
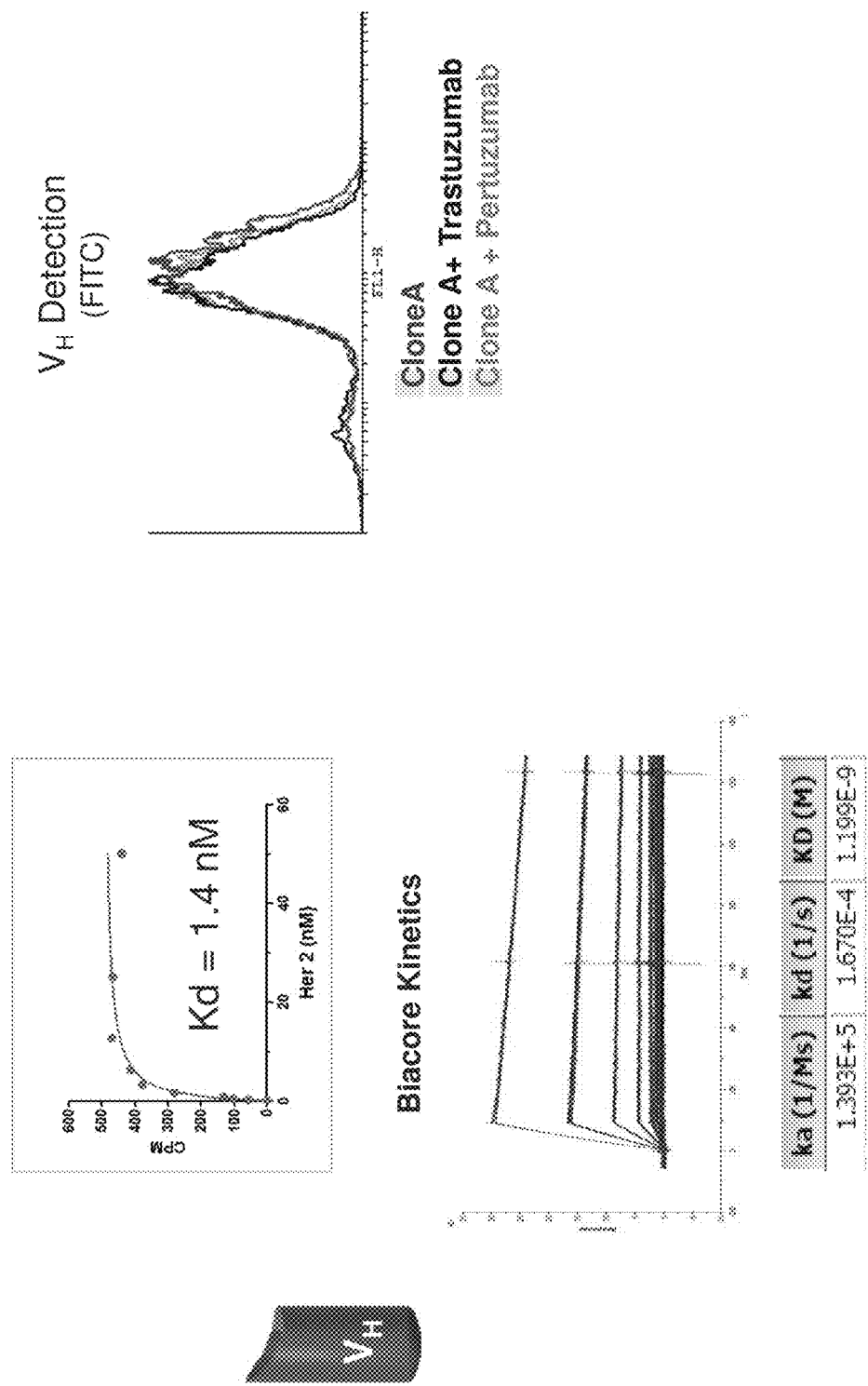
FIG. 9 shows the results of Biacore and FACS analysis of an exemplary anti-HER2 VH domain disclosed herein.

The binding kinetics of the B8 anti-HER2 VH domain (SEQ ID NO: 13) to HER2 was analyzed using a surface plasmon resonance assay (Biacore). As shown in FIG. 9, the B8 VH domain exhibited a Kd of 1.2 nM, an on-rate of $1.39 \times 10^5$ $M^{-1}s^{-1}$, and an off-rate of $1.67 \times 10^4$ $s^{-1}$.

The ability of the B8 VH domain to compete for binding with Trastuzumab and/or Pertuzumab was analyzed using a FACS-based assay. The results, set forth in FIG. 9, demonstrated that the B8 VH domain binds can bind to HER2 simultaneously with Trastuzumab and Pertuzumab. These data demonstrates that the anti-HER2 VH domain binds to a different epitope on HER2 than both Trastuzumab and Pertuzumab.

Figure 10:
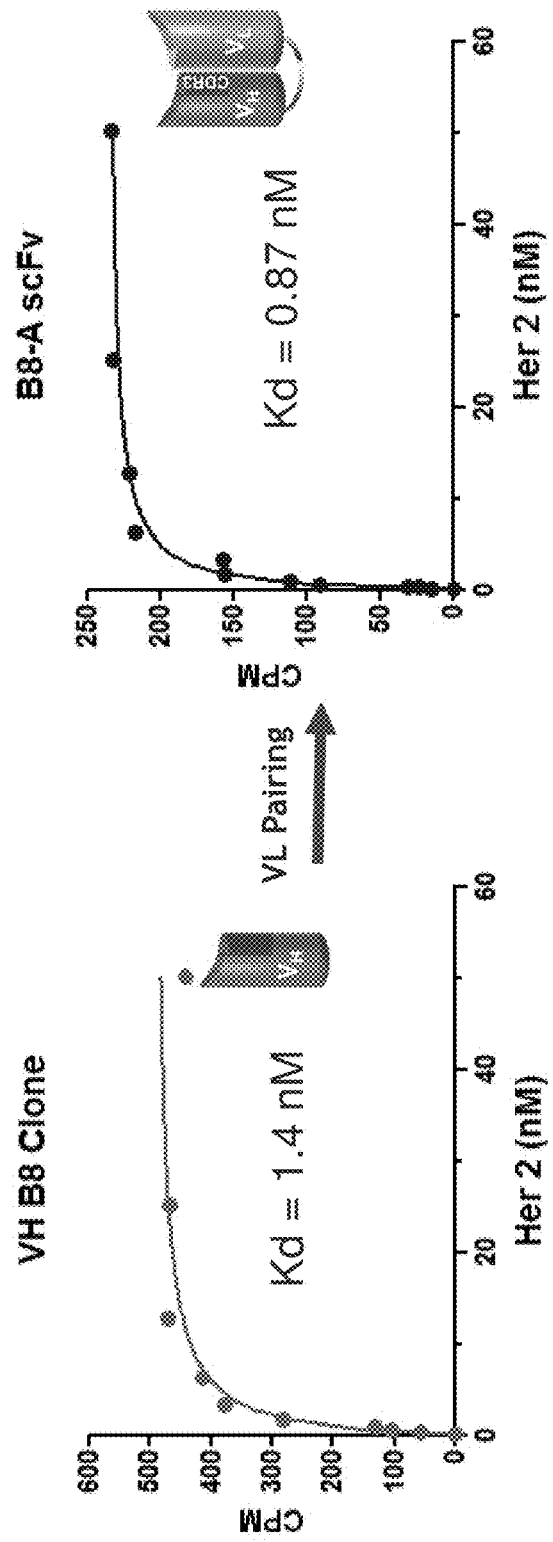
FIG. 10 shows the results of Biacore and FACS analysis of an exemplary anti-HER2 VH domain and scFv derivative disclosed herein.

The B8 VH domain was reformatted into a scFv and the binding affinity for HER2 was determined. The results set forth in FIG. 10 shows that the B8 scFv exhibited a Kd of 0.87 nM.

Example 5

Cell Proliferations Assays

Figure 11:
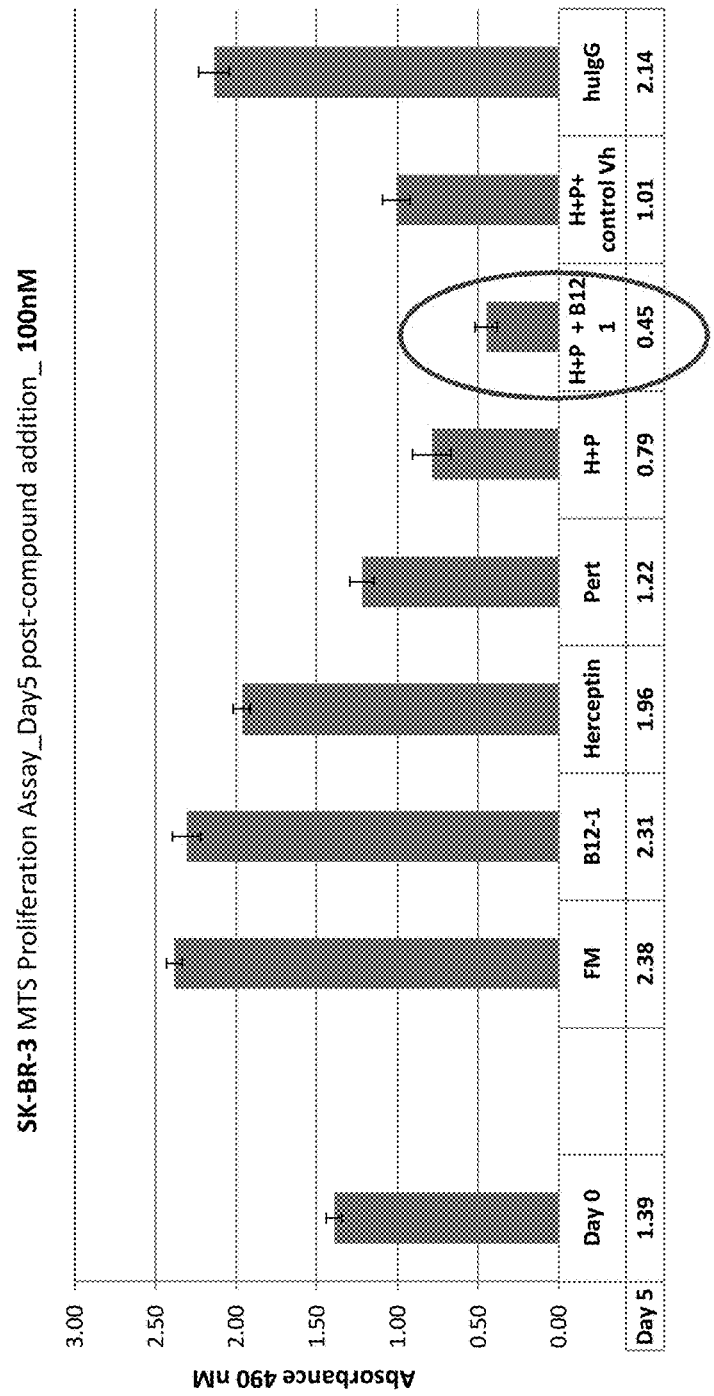
FIG. 11 shows the results of a MTS cell proliferation assay measuring the effect of anti-HER2 VH B12, trastuzumab, pertuzumab, and combinations thereof on the proliferation of SK-BR-3 cells.

The ability of the B 12 anti-HER2 VH domain (SEQ ID NO: 14), trastuzumab, or pertuzumab, either alone or in combination, to inhibit proliferation of SK-BR-3 cells was determined using an MTS cell proliferation assay. The results, set forth in FIG. 11, showed that the combination of B12 VH, trastuzumab, and pertuzumab resulted in greater inhibition of cell proliferation than was obtained with each agent alone, or with a combination of only trastuzumab and pertuzumab. These data demonstrate that B 12 VH can be used to augment the cell proliferation inhibition of trastuzumab and pertuzumab.

We claim:

1. An isolated antigen-binding polypeptide that specifically binds to human HER2, comprising a VH domain comprising an amino acid sequence selected from the group consisting of SEQ ID NOs: 13, 14, 15, and 16.

2. A pharmaceutical composition comprising the antigen-binding polypeptide of claim 1 and a pharmaceutically acceptable carrier.

3. An isolated bi-specific antigen-binding polypeptide that is capable of binding to human PDGFRβ and human HER2, comprising an antibody heavy chain comprising a first VH domain that specifically binds to human PDGFRβ, C-terminally linked to a second VH domain that specifically binds to human HER2,
   wherein the first VH domain comprises the amino acid set forth in SEQ ID NO: 24, and
   wherein the second VH domain comprises an amino acid sequence selected from the group consisting of SEQ ID NOs: 13-16.

4. The antigen-binding polypeptide of claim 3, wherein the antibody heavy chain is genetically linked to the second VH domain through an amino acid linker.

5. The antigen-binding polypeptide of claim 4, wherein the linker comprises the amino acid sequence set forth in SEQ ID NO: 23.

6. The antigen-binding polypeptide of claim 3, further comprising an antibody light chain, the light chain comprising a VL domain that specifically binds to an antigen, wherein the heavy and light chains are naturally paired.

7. An antigen-binding polypeptide comprising a dimer of two antigen-binding polypeptides of claim 3.

8. The antigen-binding polypeptide of claim 6, wherein the VL domain comprises the amino acid sequence set forth in SEQ ID NO: 28.

9. A pharmaceutical composition comprising the antigen-binding polypeptide of claim 3 and a pharmaceutically acceptable carrier.

* * * * *